United States Patent [19]
Miller et al.

[11] Patent Number: 5,922,898
[45] Date of Patent: Jul. 13, 1999

[54] PROCESS FOR PREPARING BIARYL COMPOUNDS

[75] Inventors: Joseph Arthur Miller, Scotts Valley; Robert Patrick Farrell, Mountain View, both of Calif.

[73] Assignee: Catalytica Pharmaceuticals, Inc., Mountain View, Calif.

[21] Appl. No.: 08/966,335

[22] Filed: Nov. 7, 1997

Related U.S. Application Data

[63] Continuation-in-part of application No. 08/825,792, Apr. 8, 1997, abandoned.

[51] Int. Cl.[6] .................. C07C 253/30; C07C 69/76; C07C 45/67; C07D 213/85; C07D 213/73

[52] U.S. Cl. .................. 558/378; 546/286; 546/311; 549/491; 560/102; 568/316

[58] Field of Search .................. 546/286, 311; 558/378; 560/102; 568/316

[56] References Cited

U.S. PATENT DOCUMENTS

| | | | |
|---|---|---|---|
| 4,263,466 | 4/1981 | Colon et al. | 585/421 |
| 4,620,025 | 10/1986 | Sletzinger et al. | 558/401 |
| 4,912,276 | 3/1990 | Puckette | 585/425 |
| 4,916,227 | 4/1990 | Puckette | 546/259 |
| 5,128,355 | 7/1992 | Carini et al. | 514/381 |
| 5,130,439 | 7/1992 | Lo et al. | 548/110 |
| 5,288,895 | 2/1994 | Bousset et al. | 558/378 |
| 5,364,943 | 11/1994 | Rosen et al. | 546/223 |
| 5,559,277 | 9/1996 | Beller et al. | 585/469 |

FOREIGN PATENT DOCUMENTS

| | | | |
|---|---|---|---|
| 0470794A1 | 8/1991 | European Pat. Off. | C07C 255/50 |
| 0470795A1 | 8/1991 | European Pat. Off. | C07C 255/50 |

OTHER PUBLICATIONS

File CAPLUS on STN® International Chemical Abstracts Service, (Columbus, Ohio), Accession No. 1996:707536, Japan Kokai Tokkyo Koho JP08–231454, published Sep. 10, 1996, abstract.

Sainsbury, "Modern Methods of Aryl–Aryl Bond Formation", Tetrahedron Report No. 98, Tetrahedron vol. 36, 1980, 3327 to 3359.

Bringmann et al., "The Directed Synthesis of Biaryl Compounds: Modern Concepts and Strategies", Angew. Chem, Int. Ed. Engl., vol. 29, (1990), 977–991.

Meyers et al., "Nucleophilic Aromatic Substitution on o–(Methoxy)aryloxazolines. A Convenient Synthesis of o–Alkyl–, o–Alkylidene–, and o–Arylbenzoic Acids", J. Org. Chem. vol. 43 (1978), pp. 1372–1379.

Carini et al., "Nonpeptide Angiotensin II Receptor Antagonists: The Discovery of a Seriew of N–(Bipheynylymethyl)imidazoles as Potent, Orally Active Antihypertensives", J. Med, Chem., vol. 34 (1991), 2525–2547.

Tamao et al., "Nickel–Phosphine Complex–Catalyzed Grignard Coupling. I. Cross–Coupling of Alkyl, Aryl, and Alkenyl Grignard Reagents with Aryl and Alkenyl Halides: General Scope and Limitations", Bull. Chem. Soc. Japan, vol. 49 (1976), pp. 1958–1969.

Grushin et al., "Transformations of Chloroarenes, Catalyzed by Transition–Metal Complexes", Chem. Rev., vol. 94 (1994), pp. 1047–1062.

Clough et al., "Coupling of Nonequivalent Aromatic Rings by Soluble Nickel Catalysts. A General Route to the 1,8–Diarylnaphthalenes$_{1a}$", J. Org. Chem., vol. 41 (1976), pp. 2252–2255.

Pridgen et al, "Oxazolines. 3. Regioselective Synthesis of 2–(Monosubstituted phenyl) and/or Unsymmetrically 2–(Disubstituted phenyl) 2–Oxazolines by Cross–Coupling Grignard Reagents to (Haloaryl)–2–oxazolines", J. Org. Chem., vol. 47 (1982), pp. 4319–4323.

Negishi et al., "Selective Carbon–Carbon Bond Formation via Transition Metal Catalysis. 3. A Highly Selective Synthesis of Unsymmetrical Biaryls and Diarylmethanes by the Nickel– or Palladium–Catalyzed Reaction of Aryl– and Benzylzine Derivatives with Aryl Halides", J. Org. Chem. vol. 42 (1977), pp. 1821–1823.

Zhu et al., "The Direct Formation of Functionalized Alkyl(aryl)zinc Halides by Oxidative Addition of Highly Reactive Zinc with Organic Halides and Their Reactions with Acid Chlorides, $\alpha,\beta$–Unsaturated Ketones, and Allylic, Aryl, and Vinyl Halides", J. Org. Chem. vol. 56 (1991), pp. 1445–1453.

Silbille et al., "Electrochemical Conversion of Functionalised Aryl Chlorides and Bromides to Arylzinc Species", J. Chem. Soc. Chem. Comm., 1992, pp. 283–284.

Mantlo et al., "Potent, Orally Active Imidazo[4,5–b]pyridine–Based Angiotensin II Receptor Antagonists", J. Med. Chem., vol. 34 (1991), pp. 2919–2922.

Percec et al., "Aryl Mesylates in Metal Catalyzed Homo– and Cross–Coupling Reactions. 4. Scope and Limitations of Aryl Mesylates in Nickel Catalyzed Cross–Coupling Reactions", J. Org. Chem. 1995, 60, 6895–6903.

Zembayashi et al., "Nickel–Phosphine Complex–Catalyzed Homo Coupling of Aryl Halides in the Presence of Zinc Powder", Tetrahedron Letters No. 47, (1977) pp. 4089–4092.

(List continued on next page.)

*Primary Examiner*—Michael G. Ambrose
*Attorney, Agent, or Firm*—Al A. Jecminek; John H. Grate

[57] ABSTRACT

The present invention provides a process for preparing biaryl compounds comprising reacting an arylmetal reagent selected from arylmagnesium reagents and aryllithium reagents with an arylhalide in the presence of a catalyst system comprising a catalyst selected from nickel catalysts and palladium catalysts and a cocatalyst selected from zinc cocatalysts and cadmium cocatalysts. The present invention specifically provides a process for the preparation of 2-(4'-methylphenyl)benzonitrile comprising reacting a 4-methylphenylmagnesium reagent with a 2-halobenzonitrile in the presence of a catalyst system comprising a catalyst selected from nickel catalysts and palladium catalysts and a zinc cocatalyst.

17 Claims, No Drawings

OTHER PUBLICATIONS

Colon et al., "Coupling of Aryl Chlorides by Nickel and Reducing Metals", J. Org. Chem., vol. 51 (1986), pp. 2627–2637.

Kageyama et al., "Nickel–Catalyzed Cross–Coupling Reaction of Aryl Halides in Pyridine. A Practical Synthesis of 4'–Methylbiphenyl–2–carbonitrile As a Key Intermediate of Angiotensine II Receptor Antagonists", Synlett, 1994, pp. 371–372.

Miyaura et al, "The Palladium–Catalyzed Cross–Coupling Reaction of Phenylboronic Acid with Haloarenes in the Presence of Bases", Synthetic Communications vol. 11 (1981), 513.

Ali et al., "Palladium–Catalysed Cross–Coupling Reactions of Arylboronic Acids with Π–Deficient Heteroaryl Chlorides", Tetrahedron, vol. 48 (1992), pp. 8117–8126.

Saito et al., "A Synthesis of Biaryls via Nickel(O)–Catalyzed Cross–Coupling Reaction of Chloroarenes with Phenylboronic Acids", Tetrahedron Letters, vol. 37 (1996), pp. 2993–2996.

Kalinin et al., "Carbon–Carbon Bond Formation in Heterocycles Using Ni– and Pd–Catalyzed Reactions", Synthesis, 1992, 413–432.

ial application of U.S. patent application Ser. No. 08/825,792 filed Apr. 8, 1997, now abandoned, which is incorporated by reference entirely.

PROCESS FOR PREPARING BIARYL COMPOUNDS

CROSS-REFERENCE TO RELATED APPLICATION

This patent application is a continuation-in-part of U.S. patent application Ser. No. 08/825,792 filed Apr. 8, 1997, now abandoned, which is incorporated by reference entirely.

FIELD OF THE INVENTION

This invention relates generally to preparing biaryl compounds by aryl-aryl coupling reactions. More specifically, it relates to preparing biaryl compounds by reacting an aryl-metal reagent with an aryl halide. Biaryl compounds are valuable as fine chemicals for liquid crystals and related applications and as precursors to pharmaceutically active compounds. In particular, 2-(4'-methylphenyl)benzonitrile (also known as 4-methyl-2'-cyano-biphenyl) can be used as an intermediate in the preparation of various angiotensin II antagonists.

BACKGROUND OF THE INVENTION

The following references give reviews of methods of preparing biaryl compounds: Sainsbury, *Tetrahedron*, vol. 36 (1980), pp. 3327–3359 and Bringman et al., *Angew. Chem. Int. Ed. Engl.*, vol. 29, (1990), 977–991.

In the Meyers oxazoline method to make unsymmetrical biaryl 2-carboxylic acid derivatives, disclosed in Meyers et al, *J. Org. Chem.*, vol. 43 (1978), pp. 1372–1379, the carboxyl group in 2-methoxybenzoic acids is converted into an oxazoline to activate the 2-methoxy group for nucleophilic substitution by arylmagnesium halide or aryllithium reagent amd to protect the carboxyl group in a form that is not subject to nucleophilic attack by the aryl carbanion species.

Carini et al., *J. Med. Chem.*, vol. 34 (1991), 2525–2547 disclose the application of the Meyers oxazoline method to the preparation of 2-(4'-methylphenyl) benzonitrile by the following steps: 1) 2-methoxybenzoic acid is reacted with thionyl chloride; 2) the acyl chloride formed is treated with 2-amino-2-methyl-1-propanol, which provides an amide in the crude form; 3) this amide is subjected to the action of thionyl chloride, forming 4,4-dimethyl-2-(2-methoxyphenyl)-oxazoline (yield 88% from the acid chloride); 4) this oxazoline derivative is reacted with p-tolyl-magnesium bromide and the complex formed is hydrolyzed, which gives 4,4-dimethyl-2-(4'-methylbiphenyl- 2'-yl)-oxazoline (yield 91%); and 5) the oxazoline derivative formed is then treated with phosphorus oxychloride, which finally provides 2-(4'-methylphenyl)benzonitrile (yield 96%). The overall yield is 77% but this process has the disadvantage of requiring the use of 5 steps, starting from commercially available products, due to the prior formation of the dimethyloxazolinyl group and its subsequent conversion to the cyano group. U.S. Pat. No. 5,128,355 (to Carini et al.) similarly exemplifies the application of the multistep Meyers oxazoline method to the preparation of 2-(4'-methylphenyl)benzoic acid (Example 85), and the conversion of this benzoic acid to the benzonitrile (Example 89). Implicitly, these references illustrate that when an aryl magnesium reagent (in this case, p-tolyl magnesium bromide) is used directly to provide the aryl group in an arylbenzonitrile (in this case, 2-(4'-methylphenyl) benzonitrile) the nitrile group cannot be present in the substrate that is treated with the aryl magnesium reagent. It must be in a protected precursor form during the coupling process (in this case, as the dimethyloxazolinyl group).

Tamao et al., *Bull. Chem. Soc. Japan*, vol. 49 (1976), pp. 1958–1969, discloses that arylbromides can be reacted with arylmagnesium halides (aryl Grignard reagents) in the presence of dihalodiphophinenickel complexes to give biaryl compounds. A sole disclosed attempt to react an aryl chloride (chlorobenzene) with an arylmagnesium halide (mesityl) was reported to give only a 6% yield of the desired biaryl. Similar reactions of the bromobenzene with mesityl-magnesium bromide gave yields of 78–96%. This reference states, "The most serious limitation is that the substituents on the organic halides and on the Grignard reagents are restricted to those which cannot react with Grignard reagents."

In a review article titled "Transformations of Chloroarenes, Catalyzed by Transition-Metal Complexes", *Chem. Rev.*, vol 94 (1994), pp. 1047–1062, Grushin et al. state, "Unfortunately, the most reactive iodo- and bromoarenes are the most expensive ones, whereas aryl fluorides are both costly and unreactive. Chloroarenes are certainly the most attractive aryl halides for synthetic applications on an industrial scale, because they are inexpensive and readily available in bulk quantities. The main drawback here is the exceedingly high stability of the aromatic carbon-chlorine bond whose inertness remains the major obstacle on the way to wide utilization of chloroarenes."

Clough et al., *J. Org. Chem.*, vol. 41 (1976), pp. 2252–2255 discloses that 1,8-dihalonapthalenes can be reacted with arylmagnesium halides in the presence of certain soluble nickel catalysts to give 1,8-diarylnaphthalenes. The reactivities of the 1,8-dihalonaphthalenes in this system was found to be I>Br>>Cl.

U.S. Pat. No. 4,912,276 discloses that aryl chlorides can be reacted with arylmagnesium halides in the presence of a nickel-triorgandphosphine catalyst to give biaryl compounds. The disclosed scope of the aryl groups in the arylchlorides, the arylmagnesium reagents, and the biaryl compounds consists of phenyl and substituted phenyl with hydrocarbyl or hydrocarbyloxy substituents or protected carbonyl-containing derivatives thereof. These are all substituents that are unreactive to arylmagnesium halides. The only biaryl whose preparation is exemplified by working examples is the symmetrical biaryl 2,2'dimethylbiphenyl, prepared from 2-chlorotoluene and o-tolylmagnesium chloride (derived from 2-chlorotoluene).

Pridgen, *J. Org. Chem.*, vol. 47 (1982), pp. 4319–4323 discloses two examples in which 2-(chlorophenyl)-2-oxazolines are reacted with arylmagnesium halides in the presence of a diphosphine-chelated nickel catalyst to give the corresponding 2-(biaryl)-2-oxazoline compounds. The oxazoline group activates the aryl chloride and provides a form of the carboxyl group that is protected from reaction with the arylmagnesium halide.

U.S. Pat. No. 5,288,895 discloses a process for the preparation of 4-methyl-2'-cyanobiphenyl (a.k.a. 2-(4'-methylphenyl)benzonitrile) wherein a 2-halobenzonitrile is reacted with a 4-methylphenylmagnesium halide in the presence of manganous salt. The Examples of this patent, which describe reactions of 2-chlorobenzonitrile, report analyzed chemical yields of 60–75% of 2-(4'-methylphenyl) benzonitrile) in a recovered "brown viscous liquid". Recrystallizations (plural) give the product as a beige solid, but the yields of these purified solids are not reported.

This patent also discloses tests showing that the direct reaction of 4-methylphenylmagnesium bromide with 2-chlorobenzonitrile, in the absence of manganese salt, "proves incapable of giving 4-methyl-2'-cyanobiphenyl". Analysis showed unreacted 2-chlorobenzonitrile and the addition product of the reagent to the nitrile group, 2-chloro-1-phenyl(4-tolyl)ketone, but no trace of 2-(4'-methylphenyl) benzonitrile.

This patent also discloses attempted reactions of several equivalents of 4-methylphenylmagnesium bromide with 1 equivalent of 2-broinobenzonitrile and 0.3 equivalents of either $PdCl_2$ or $NiCl_2$ in tetrahydrofuran at 0° C. Yields of 22% and 27%, respectively, of 2-(4'-methylphenyl) benzonitrile were analyzed in recovered crude residue. Similar reactions with 0.003 equivalents tetrakis (triphenylphosphine)palladium(0) at 0 and 65° C. gave only a 1% yield in the residue.

International Patent Application PCT/IB97/00266 (International Publication Number WO 97/30970) discloses that palladium catalyzed reactions of arylmagnesium halides (including 4-methylphenylmagnesium halides) with bromobenzonitriles give improved selectivity to the arylbenzonitrile vs. the benzophenone imine product formed by reaction of the arylmagnesium halide at the nitrile group when the arylmagnesiumn halide is added to the bromobenzonitrile slowly. The claims call for addition times of at least 30 minutes. The working examples illustrating the invention, however, are limited to addition times of at least 2 hours. For reaction of 4-methylphenylmagnesium chloride with 2-bromobenzonitrile with an addition time of 2 hours, the ratio of 2-(4'-methylphenyl)benzonitrile to the benzophenone imine product is 5:1 (Example 10). Better ratios, 10:1 and greater, from this reaction are reported in working examples with addition times of 8 hours or longer (Examples 9, 11 and 12).

Riguet et al., Tetrahedron Letters, vol. 38 (1997), pp. 4397–4400 discloses reactions of aryl manganese chlorides with aryl iodides, bromides, or triflates in the presence of palladium complexes to produce various functionalized unsymmetrical biaryls. The reference reports the formation of 4-(4'-methylphenyl)benzonitrile in 91% isolated yield from 4-methylphenylmanganese chloride and 4-bromobenzonitrile by the disclosed procedure.

Negishi et al, J. Org. Chem., vol. 42 (1977), pp. 1821–1823 discloses reactions of arylzinc derivatives (arylzinc chloride or diarylzinc) with aryl bromides or iodides in the presence of nickel or palladium complexes as catalysts to produce unsymmetrical biaryls. The arylzinc derivatives were prepared by a metathesis reaction between the corresponding aryllithium and zinc dichloride. The reference does not report any attempt to react an arylzinc derivative with an aryl chloride and is silent as to whether aryl chlorides are suitable or unsuitable as alternatives to the aryl bromides or iodides. The authors comment on the ability of arylzinc derivatives to tolerate various electrophilic functional groups, such as nitrile and ester, in the arylbromide or iodide.

Zhu et al., J. Org. Chem., vol. 56 (1991), pp. 1445–1453 similarly discloses reactions of arylzinc halides with aryl bromides or aryl iodides in the presence of a palladium tetrakis(triphenylphosphine as catalyst to form biaryl compounds. The arylzinc halides were prepared by the reaction of the arylhalide with a form of highly reactive zinc.

Silbille et al., J. Chem. Soc. Chem. Comm., 1992, pp. 283–284 discloses a reaction of 4-trifluoromethylphenylzinc chloride, prepared from 4-trifluoromethylchlorobenzene, with 4-bromobenzonitrile using the palladium complex $PdCl_2(PPh_3)_2$ as catalyst to form 4-trifluoromethylphenyl-4'-cyanobiphenyl. This reference also discloses a method of preparing arylzinc halides from arylchlorides and arylbromides, including ones bearing various functional groups such as ester, nitrile, or ketone.

Carini et al., J. Med. Chem., vol. 34 (1991), 2525–2547, cited above, discloses the preparation of 3-(4'-methylphenyl)benzonitrile by reacting 4-methylphenylzinc halide (prepared from 4-bromotoluene via 4-methylphenyl magnesium bromide, which is reacted with zinc chloride) and 3-bromobenzonitrile in the presence of bis (triphenylphosphine)nickel dichloride as precatalyst. U.S. Pat. No. 5,128,355 (to Carini et al.) similarly shows an equation (Scheme 14, Equation e) representing the nickel catalyzed cross coupling of a methylphenylzinc chloride (isomer unspecified) with a bromobenzonitrile (isomer unspecified) to give a methylphenylbenzonitrile (isomer unspecified). This method is exemplified only for the preparation of 2,6-dicyano-4'-methylbiphenyl from 2,6-dicyanophenylbromide (Example 343).

Mantlo et al., J. Med. Chem., vol. 34 (1991), pp. 2919–2922 discloses the preparation of 2-(4'-methylphenyl) benzonitrile from 4-bromotoluene and 2-bromobenzonitrile according to the method (referenced) of Negishi et al. J. Org. Chem., vol. 42 (1977), pp. 1821–1823. A zinc derivative was formed from the 4-bromotoluene and reacted with the 2-bromobenzonitrile in the presence of a catalytic amount of a dichlorobis(triphenylphosphine)nickel.

European Patent Application 470,794 discloses a process for preparing biphenylcarbonitriles in which a metal or organometallic 4-methylphenyl derivative is reacted with a bromo-, iodo-, or trifluoromethanesulphonyloxybenzonitrile in the presence of a palladium or nickel catalyst. The metal or organometallic 4-methylphenyl derivatives disclosed are of copper, lithium, tin, silicon, zirconium, aluminum, thallium, mercury, and magnesium. 4-methylphenyl derivatives of tributyltin are particularly preferred and are the only 4-methylphenyl derivatives shown by working example.

Only two of the working examples relate to the disclosed process for preparing biphenylcarbonitriles, Examples 1 and 2. Both involve reactions of the 4-methylphenyl tributyltin derivative with 2-bromobenzonitrile in the presence of tetrakis(triphenylphosphine)palladium. The 4-methylphenyl tributyltin derivatives are prepared by the reaction of the corresponding 4-methylphenyl magnesium bromide with tributyltin chloride, Followed by separation and high vacuum distillation of the 4-methylphenyl tributyltin derivative. Example 2 shows the preparation of 4'-methylbiphenyl-2-carbonitrile (a.k.a. 2-(4'-methylphenyl)benzonitrile) by this method, involving a prolonged reaction time (36 hours) for the coupling reaction.

Percec et al J. Org. Chem., vol. 60 (1995), pp. 6895–6903 discloses reactions in which certain aryl mesylates are reacted with 1.8–2.0 equiv. of certain arylmagnesium halide or arylzinc halide reagents in the presence of 1.0 equiv. of zinc powder and a nickel phosphine complex as catalyst to form unsymmetrical biaryls in yields ranging from 31–60%.

Zembayashi et al., Tetrahedon Letters, vol 47 (1977), pp. 39–4092 discloses reductive coupling of aryl bromides to the corresponding symmetrical biaryls by zinc powder in the presence of a nickel-phosphine complex as catalyst. The reference states, "Although the exact mechanism of the present coupling reaction has not yet been clarified, it seems likely that organozinc intermediates are not involved, but metallic zinc acts as a reducing agent for the Ni(II) species as mentioned above."

Colon et al., J. Org. Chem., vol. 51 (1986), pp. 2627–2637 and U.S. Pat. No. 4,263,466 (to Colon et al.) similarly discloses reductive coupling of aryl chlorides to the corresponding symmetrical biaryls by an excess of a reducing metal (Zn, Mg, or Mn) in the presence of a catalyst formed from an anhydrous nickel salt and triphenylphosphine. In an extensive exposition on the mechanism of the reaction, the authors conclude that the reducing metal serves to reduce the nickel salt and various arylnickel intermediates participating in the reaction. Nowhere do the authors make any mention of an arylzinc intermediate.

Kageyama et al., *Synlett*, 1994, pp. 371–2 discloses a procedure said to be advantageous "compared to the original Colon's method" (the reference discussed in the preceding paragraph herein) in which pyridine is used as solvent for the reductive coupling reaction affording symmetrical biaryls. (U.S. Pat. No. 5,380,910 to Kageyama also discloses this procedure.) This reference further discloses the extension of this procedure to reductive cross-coupling reactions of certain aryl halides (1 equiv.) in the presence of zinc powder (2 equiv.) and a nickel-phosphine catalyst in pyridine solvent to provide unsymmetrical biaryls. This reference is mainly concerned with the preparation of 4'-methylbiphenyl-2-carbonitrile-(also known as 2-(4'-methylphenyl) benzonitrile) by such reaction of 4-bromotoluene and 2-chlorobenzonitrile, which is reported to provide the desired unsymmetrical (cross-coupled) biaryl product in 69% yield. The two undesired symmetrical (homocoupled) biaryl byproducts are formed in 11–12% yield each. Attempted reaction of 3-chlorotoluene with 2-chlorobenzonitrile did not afford the desired cross-coupled product, nor any homocoupled bitolyl. Only a 21% yield of the homocoupled bis(benzonitrile) is reported. There is no indication in the reference that the 4-chlorotoluene reacted at all.

A frequently used method of synthesizing biaryls containing electrophilic functional groups on a laboratory scale is the palladium catalyzed cross-coupling (Suzuki coupling), in which iodoaromatics, bromoaromatics, or aryl sulfonates are reacted with arylboronic acids or boronate esters in the presence of palladium catalysts and a base. An early report of this general reaction is Miyaura et al., *Synthetic Communications* vol. 11 (1981), 513. In this reference, chlorobenzene is reported to fail to react with phenylboronic acid using tetrakis(triphenylphosphine)palladium as catalyst in this system.

Ali et al., *Tetrahedron*, vol 48 (1992), pp. 8117–8126 discloses Suzuki-type cross-coupling reactions of arylboronic acids with pi-electron deficient heteroaryl chlorides (chloropyridines, chloropyrimidines, and chloropyrazines, chloroquinolines). These authors state, "It is widely accepted that palladium-catalyzed cross coupling reactions of arylboronic acids, and indeed of other organometallic species, proceed best with aryl or heteroaryl bromides or iodides, and either poorly, or more commonly, not at all with the corresponding chlorides." These investigators confirmed early literature reports that reaction of phenylboronic acid with either chlorobenzene or 3-chloropyridine in the presence of tetrakis(triphenylphosphine) palladium failed to prcoduce any coupled product. Using Pd(bis-1,4-(diphenylphosphino)butane)Cl$_2$, however, they were able to get chlorobenzene to react to give 28% of biphenyl, and 3-chloropyridine was converted to 3-phenylpyridine in 71% yield. Among 2-chloropyridines, the reaction tolerated some (3-nitro, 5-chloro) but not other (3-OH, 3-CONH$_2$) substituents.

U.S. Pat. No. 5,130,439 discloses a process for preparing certain protected tetrazolyl biphenyls in which a protected tetrazolylphenylboronic acid or boronate derivative is reacted with a substituted phenyl bromide or iodide or a substituted sulfonyloxyphenyl derivative in the presence a base and a nickel, palladium or platinum catalyst, preferably palladium. Three of the working examples (Examples 4, 9, and 12) relate to the disclosed process for preparing the protected tetrazolyl biphenyls, and all involve reactions of triphenylmethyltetrazolylphenylboronic acid with a substituted. (4-methyl, 4-hydroxymethyl, 4-formyl) bromobenzene in the presence of a tetrakis(triphenylphosphine) palladium catalyst and a carbonate base. This process has the disadvantage of requiring prior synthesis of the triphenylmethyltetrazolylphenylboronic acid. This reference discloses a process for preparing the triphenylmethyltetrazolylphenylboronic acid from the corresponding bromobenzonitrile by reacting it with tributyltin chloride and sodium azide, then with triphenylmethyl chloride to form the triphenylmethyltetrazolylphenylbromide, which is reacted sequentially with n-butyllithium and triisopropylborate and the resulting boronate ester is finally hydrolyzed to the boronic acid. This reference illustrates that the nitrile group must be protected, in this case as the triphenylmethyltetrazolyl group, to be compatible with the use of an aryllithium intermediate in the overall process.

European Patent Application 470,795 discloses a process for preparing biphenylcarbonitriles in which a 4-methylphenyl boronic acid or boronate ester is reacted with a bromo-, iodo-, or trifluoromethanesulphonyloxybenzonitrile in the presence of a palladium or nickel catalyst and a suitable base. Three of the working examples (Examples 1, 2, and 6) relate to the disclosed process for preparing biphenylcarbonitriles, and all involve reactions of the 4-methylphenylboronic acid with 2-bromobenzonitrile in the presence of a palladium catalyst and sodium carbonate.

Saito et al., *Tetrahedron Letters*, vol. 37 (1996), pp. 2993–2996 states, "The palladium-catalyzed cross-coupling reaction of arylboronic acids with aryl halides or triflates gives biaryls. High yields have been achieved with many substrates having various functional groups on either coupling partner, when using aryl bromides, iodides, or triflates as an electrophile. Chloroarenes are an economical and easily available, but they have been rarely used for the palladium catalyzed cross coupling reaction of arylboronic acids because of the oxidative addition of chloroarenes is too slow to develop the catalytic cycle. However, chloroarenes have been an efficient substrate for the nickel catalyzed cross coupling reaction with Grignard reagents . . . developed by Kumada and Tamao." This reference (Saito et al.) discloses syntheses of unsymmetrical biaryls by a nickel(0) catalyzed reaction of arylchlorides with arylboronic acids and tripotassium phosphate as the base at elevated temperatures.

U.S. Pat. No. 5,559,277 discloses a process for preparing biaryls by the Suzuki reaction of haloaromatics or arylsulfonates with arylboronates in the presence of a base and certain specific palladium compounds as catalysts. In addition to numerous bromoaromatics, reactions of chloroacetophenone and 2-chlorobenzonitrile are shown in working examples. All the working examples use at least 50% mole excess of the arylboronate relative to the haloaromatic and conduct the reaction for 16 hours at 130° C. The disclosed process also has the disadvantage of requiring the separate preparation of the arylboronate. Example 7 describes the preparation of 2-cyano-4-methylbiphenyl (a.k.a. 2-(4'-methylphenyl)benzonitrile) from 2-chlorobenzonitrile and 4-methylphenylboronic acid in 73% yield (49% yield on the 4-methylphenylboronic acid).

Kalinin, *Synthesis*, 1992, 413–432 reviews carbon-carbon bond formation to heteroaromatics using nickel and palladium catalyzed reactions. It shows numerous examples of the formation of unsymmetrical biaryls, wherein at least one of the aryl groups includes a heteroatom, including examples of palladium catalyzed reactions of arylbromides and aryliodides with arylzinc halides, palladium catalyzed reactions of chloropyridines with arylmagnesium halides, and nickel catalyzed reactions of arylchlorides and arylbromides with arylmagnesium halides.

U.S. Pat. No. 5,364,943 discloses the preparation of 3-amino-2-phenylpyridine and two 3-(substituted benzylamino)-2-phenylpyridine derivatives by the reaction of the corresponding 3-amino-2-chloropyridine or N-benzyl derivative with phenyl magnesium bromide in the presence of bisphosphine)nickel dichloride complexes. For the parent compound (Example 7), a total of 4.4 eq. of phenylmagnesium bromide was reacted with 3-amino 2-chloropyridine and 0.5 eq. [bis(diphenylphosphino)ethane] nickel(II) chloride over the course of two days, to ultimately obtain a 48% of the isolated product.

Copending parent U.S. patent application Ser. No. 08/825, 792 filed Apr. 8, 1997, of which the present patent application is a continuation-in-part, discloses a process for preparing biaryl compounds comprising reacting an arylzinc reagent with an arylchloride in the presence of a nickel catalyst or a palladium catalyst. The parent application further discloses a process wherein the arylzinc reagent is prepared by reacting a zinc salt with a arylmagnesium reagent or an aryllithium reagent. It teaches that the arylzinc reagent is prepared using a stoichiometric amount of zinc salt relative to the arylmagnesium or aryl lithium reagent, stating, "Preferably, the zinc salt is reacted with one to two equivalents of aryllithium or arylmagnesium reagent to form the arylzinc salt, the diarylzinc compound, or mixtures thereof. It further teaches reacting a stoichiometric amount of arylzinc reagent with the arylchloride, stating, "Either reactant may be the limiting reactant and this choice can respond to other considerations, such as which is the more costly reactant to provide and which homocoupled by-product is more readily separated or removed to an acceptable level from the desired cross-coupled product. Generally the ratio of equivalents of arylzinc reagent to mole of arylchloride ranges from 0.5:1 to 2:1. One mole of diarylzinc reagent is counted as two equivalents of arylzinc reagent. In typical embodiments, this ratio is in the range 1:1 to 1.5:1." Taken as a whole, the parent application teaches the preparation of the arylzinc reagent as a distinct step from reacting the arylzinc reagent with the arylchloride. Nowhere does the parent application suggest reacting an arylmagnesium reagent or arylithium reagent with an arylhalide in the presence of a nickel catalyst or a palladijum catalysts with zinc present in the reaction mixture.

OBJECTS OF THE INVENTION

The object of this invention is to provide an economically preferable, effective and efficient process for the preparation biaryl compounds. Further objects of this invention are to provide such a process having one or more of the following characteristics: 1) Capable of preparing unsymmetrical biaryl compounds bearing one or more reactive functional substituents on one of the aryl groups. 2) Capable of providing the biaryl compounds in high yields from arylhalide raw materials. 3) Capable of using inexpensive arylchlorides as reactants, rather than requiring arylbromides or aryliodides. 4) Minimizes the number of process reaction steps. 5) Minimizes the number of other process operations, including avoiding any need to isolate process intermediates, with attendant yield losses and other costs. 6) Readily scaleable for the production of commercial-scale quantities (10's to 10,000's of Kgs) of biaryl compounds. Other objects and advantages will become apparent to persons skilled in the art and familiar with the background references from a careful reading of this specification.

SUMMARY OF THE INVENTION

In its most basic terms, the present invention provide a process, having practical utility, for preparing biaryl compounds of the formula Ar-Ar', wherein Ar and Ar' are aryl groups and may be identical or different, comprising reacting an arylmetal reagent selected from arylmagnesium reagents and aryllithium reagents, wherein the aryl group is Ar, with an arylhalide of the formula Ar'X, wherein X is a halide, in the presence of a catalyst system comprising a catalyst selected from nickel catalysts and palladium catalysts and a cocatalyst selected from zinc cocatalysts and cadmium cocatalysts. The invention further provides a process for preparing biaryl compounds that is compatible with a variety of reactive functional substituents in the Ar' group of aryl halide and the biaryl compound, avoiding costs associated with protecting and deprotecting such substituents, by providing a catalyst system that promotes selective formation of the desired biaryl compound in preference to the undesired direct reaction of the arylmetal reagent with the reactive functional substituents. The present invention is thereby particularly advantageous for preparing unsymmetrical biaryl compounds in which the Ar' group, but not the Ar group, contains a functional substituent that is reactive to the arylmetal reagent.

The invention also provides a process that, for many biaryl compounds, is capable of using inexpensive arylchlorides as reactants, rather than requiring arylbromides or aryliodides to provide the Ar' group in the biaryl compound.

In certain embodiments of the present invention, an arylhalide comprising the Ar group is reacted with magnesium to form the arylmagnesium reagent. In certain of these embodiments, the arylhalide used to produce the arylmagnesium reagent is an arylchloride of the formula ArCl. The invention thereby provides a process for preparing biaryl compounds in which arylchloride reactants, ArCl and Ar'Cl, are used to provide each aryl group in the biaryl compound.

The present invention also provides a process capable of providing high yields of the desired biaryl compounds based on the arylhalide. Yields are typically above about 50% based on the arylhalide, preferably above about 60%, more preferably above about 70%.

In a specific preferred embodiment, the present invention provides a process for the preparation of 2-(4'-methylphenyl)benzonitrile comprising reacting a 4-methylphenylmagnesium reagent with a 2-halobenzonitrile, most preferably 2-chlorobenzonitrile, in the presence of a catalyst system comprising a catalyst selected from nickel catalysts and palladium catalysts and a zinc cocatalyst. The 4-methylphenylmagnesium reagent may be produced from 4-methylphenylchloride by its reaction with magnesium. The invention thereby provides an efficient process for the preparation of 2-(4'-methylphenyl) benzonitrile from 4-methylphenylchloride and 2-chlorobenzonitrile.

DETAILED DESCRIPTION OF THE INVENTION

The present invention provides a process for the preparation of biaryl compounds of the formula Ar-Ar', wherein Ar and Ar' are aryl groups and may be identical or different.

Suitable aryl groups Ar and Ar' include carbocyclic aryl groups, having only carbon atoms in the aromatic ring system and heterocyclic aryl groups, having one or more heteroatoms in the aromatic ring system. Typical carbocyclic aryl groups have 6–14 carbon atoms in the aromatic ring system. Preferred carbocyclic groups are phenyl and substituted phenyl groups. Typical heterocyclic aryl groups have 5–13 atoms in the aromatic ring system which comprises carbon atoms and one or more heteroatoms. Preferred heteroatoms are oxygen, sulfur, and nitrogen. Preferred heterocyclic aryl groups have 5 or 6 atoms in an aromatic ring comprising one or more heteroatoms selected from the group oxygen, sulfur, and nitrogen, benz-fused derivatives thereof, and substituted derivatives thereof. Examples of preferred heterocyclic aryl groups include pyridyl, furyl, thiophenyl, pyrrolyl, their benz-fused derivatives quinolinyl, isoquinolinyl, benzfuryl, benzthiophenyl, indolyl, isoindolyl, and substituted derivatives thereof.

Suitable substituents in substituted aryl groups Ar are unreactive towards the arylmetal reagent and include alkyl (preferably $C_1$–$C_{12}$), alkenyl (preferably $C_2$–$C_{12}$), alkynyl (preferably $C_3$–$C_{12}$), alkoxy preferably $C_1$–$C_{12}$), aryloxy, aryl, heteroaryl, F, Cl, $SO_2$, SOR, N-dialkyl (preferably $C_1$–$C_{12}$), and Si-trialkyl (preferably $C_1$–$C_{12}$).

Suitable substituents in substituted aryl groups Ar' include those suitable in Ar and further include ethynyl, acyloxy preferably $C_1$–$C_{12}$), OH, $NO_2$, CN, COOH, CHO, $SO_3H$, $NH_2$, NH-alkyl (preferably $C_1$–$C_{12}$), NHCO-alkyl (preferably $C_1$–$C_8$), CONH-alkyl (preferably $C_1$–$C_4$), CON-dialkyl (preferably $C_1$–$C_4$), COO-alkyl (preferably $C_1$–$C_{12}$), $CONH_2$, CO-alkyl (preferably $C_1$–$C_{12}$), NHCOH, NHCOO-alkyl (preferably $C_1$–$C_8$), CO-aryl, COO-aryl, $CHCHCO_2$-alkyl (preferably $C_1$–$C_{12}$), $CHCHCO_2H$, PO-diaryl, PO-dialkyl Preferably $C_1$–$C_8$), and trihalomethyl. It will be recognized by those skilled in the art that substituents with an active hydrogen (for example ethynyl, OH, COOH, $SO_3H$, $NH_2$,) will consume an extra equivalent of arylmetal reagent, but that the resulting metal salt of the substituted arylhalide may proceed to react to form the biaryl compound.

Suitable halides for the arylhalide, Ar'X, are chloride, bromide, and iodide. For economic reasons, chloride and bromide are generally preferred, and chloride is generally most preferred. For reactivity reasons, however, bromide and iodide may be more practical in certain embodiments.

Suitable arylmagnesium reagents are selected from the group consisting of arylmagnesium salts, diarylmagnesium compounds, or mixtures thereof. Arylmagnesium salts have the general formula ArMgY, wherein Ar is an aryl group and Y is an inorganic or organic salt anion. The identity of the anion Y is not critical but it must not interfere with the reaction, which can be determined by routine experimentation. Preferred arylmagnesium salts are arylmagnesium halides, also known as aryl Grignard reagents, of the general formula ArMgX, wherein X is a halide anion. Especially preferred are arylmagnesium chloride and arylmagnesium bromide reagents. Diaryl magnesium compounds have the general formula $Ar_2Mg$. Arylmagnesium halides and diarylmagnesium compounds can be prepared from arylhalides and magnesium by methods known in the art.

Suitable aryllithium reagents are aryllithium compounds of the general formula ArLi, wherein Ar is an aryl group. Aryllithium compounds can be prepared by methods known in the art.

Suitable nickel and palladium catalysts for the process of the invention include those provided by nickel and palladium compounds and salts, in particular nickel(0) and palladium(0) compounds and nickel(II) and palladium(II) compounds and salts. Preferably, the catalyst also comprises a ligand. Suitable ligands include monodentate, bidentate, and tridentate ligands comprising nitrogen or phosphorus as ligating atom. Preferred ligands are triorganophosphine, triorganophosphite, and aromatic nitrogen heterocycle ligands. Examples of preferred ligands include triarylphosphines (e.g. triphenylphosphine), bidentate bis (diarylphosphino) compounds (e.g. 1,1'-bis-(diphenylphosphino)ferrocene), trialkylphosphites (e.g. triisopropylphosphite), and pyridine-type ligands (e.g. pyridine, bipyridine). Particular ligands include those illustrated in the working Examples herein.

Suitable and optimal ratios of the ligand to catalyst metal depend on a number of other parameters, including the catalyst metal, whether nickel or palladium, the identity of the ligand, the concentration of the catalyst, the reaction temperature, the reactivity of the reactants, the solvent, and the like, and can be readily determined by routine experimentation. Typically the ratio of the ligand to the catalyst metal is in the range of 1:1 to 4:1. However, the amount of ligand in the reaction mixture may be in excess of the maximum ratio that could be bound to the catalyst metal.

The active catalyst may be prepared in advance of its introduction to the reaction mixture, or may be generated in the reaction mixture. It is believed that the active catalyst in the reaction is a nickel(0) or palladium(0) compound. The active catalyst may be provided by a preformed ligated nickel(0) or palladium(0) compound (e.g. tetrakis (triphenylphosphine)palladium(0), bis(triphenylphosphine) nickel(0) dicarbonyl) or may be provided by combining in solution, either ex situ or in situ to the reaction mixture, a suitable ligand with a suitable nickel(0) or palladium(0) source (e.g. bis(1,5-cyclooctadiene)nickel(0), tris (dibenzylideneacetone)palladium(0)). When the catalyst is provided by a nickel(II) or palladium(II) compound or salt, the active catalyst is provided by its reduction either ex situ or in situ to the reaction mixture. Generally, the arylmetal reagent is capable of reducing the nickel(II) or palladium(II) to generate the active catalyst in situ, with concomitant generation of the symmetrical biaryl Ar-Ar. This can be determined by routine experimentation. Suitable reductants for ex situ generation of the active catalyst from nickel(II) and palladium(II) sources are known in the art and include organomagnesium halide reagents, (e.g. methylmagnesium halide) and various hydride reagents (e.g. sodium bis(2-methoxyethoxy)aluminum dihydride). Preferably the nickel (II) or palladium(I) is combined with ligand prior to its reduction. The nickel(II) or palladium(II) may be provided as a preformed ligated nickel(II) or palladium(II) compound (e.g. dichlorobis(triphenylphosphine)nickel(II), dichloro[1, 1'-bis(triphenylphosphino)ferrocene]palladium(II)) or may be provided by combining in solution a suitable ligand with a suitable nickel(I) or palladium(I) compound (e.g. dichlorobis(acetonitrile)palladium(II)) or salt. Suitable nickel(II) and palladium(II) salts include the salts having the general formula $NiY_2$ and $PdY_2$, wherein Y is defined as above. Preferred nickel(II) or palladium(II) salts include the chlorides, bromides, carboxylates (e.g. formate, acetate, stearate) and acetylacetonates. Generally, anhydrous nickel and palladium salts are preferred. In certain embodiments, however, it has been surprisingly found that a small amount of water in the salt can be beneficial to the catalyst activity. Whether an amount of water is beneficial or detrimental in a specific embodiment can be determined by routine experimentation.

Suitable zinc cocatalysts for the present invention are those provided by zinc metal, zinc salts, and zinc compounds. Preferred forms of zinc metal include zinc dust and zinc powder. Suitable zinc salts include salts having the general formula $ZnY_2$, wherein Y is defined as above. Preferred zinc salts are the zinc halides $ZnX_2$, wherein X is a halide ion. Especially preferred are zinc chloride and zinc bromide. Also preferred are zinc carboxylate .alts such as zinc acetate. Suitable zinc compounds include compounds of the general formula RZnY and $R_2Zn$, wherein R is an organo group which does not interfere with the reaction and Y is as defined above.

Suitable cadmium cocatalysts for the present invention are those provided by cadmium metal, cadmium salts, and cadmium compounds. Suitable cadmium salts and cadmium compounds are analogous to the suitable zinc salts and zinc compounds defined above, substituting cadmium for zinc. Because of the toxicity of cadmium, zinc cocatalysts are generally preferred.

The reaction of the arylmetal reagent with the arylhalide may be conducted without solvent or with an additional solvent that is reaction-inert. By reaction-inert solvent is meant a solvent system which does not react with the reactants or products of the reaction, or react unfavorably with the catalyst. The term solvent system is used to indicate that a single solvent or a mixture of two or more solvents can be used. Representative solvents are aromatic hydrocarbons such as benzene, toluene, xylene; aliphatic hydrocarbons such as pentane, hexane, heptane; acetonitrile; dialkyl ethers; and cyclic ethers, and mixtures thereof. The solvent system used need not bring about complete solution of the reactants.

Preferred solvents in the solvent system are ether solvents, including diethyl ether, diisopropyl ether, dibutylether, methyl-t-butylether, dimethoxyethane, diglyme, dibutyldiglyme, tetrahydrofuran, dioxane, and the like. It is generally preferred that the solvent system is anhydrous. In certain embodiments, however, it has been surprisingly found that a small amount of water, typically in a 1:2 to 2:1 mole ratio to the catalyst, can be beneficial to the catalyst activity. Whether small amounts of water are advantageous or detrimental in a specific embodiment can be determined by routine experimentation.

The ratio of the arylmetal reagent to the arylhalide is not critical. Either reactant may be the limiting reactant and this choice can respond to other considerations, such as which is the more costly reactant to provide and which homocoupled by-product is more readily separated or removed to an acceptable level from the desired cross-coupled product . Generally the ratio of equivalents of arylmetal reagent to mole of arylhalide ranges from 0.5:1 to 2:1. (One mole of diarylmagnesium reagent is counted as two equivalents of arylmagnesium reagent.) In typical embodiments, this ratio is in the range 1:1 to 1.5:1. A modest excess of arylmetal reagent over arylhalide is often preferred to compensate for side reactions that nonselectively deplete the arylmetal reagent; for example, homocoupling (to symmetrical Ar-Ar) and reaction with a functional substituent on the Ar' group of the arylhalide and the biaryl product.

The catalyst and cocatalyst in the catalyst system are each present in catalytic amounts, meaning less than stoichiometric relative to the reactants. The mole ratio of the catalyst to the arylhalide to be reacted is not critical, but should be a catalytic ratio of about 1:10 or less. The minimum amount of catalyst relative to the arylhalide depends on the activity of the specific catalyst composition, the specific arylhalide and arylmetal reagent to be reacted, the reaction temperature, the concentration of the reactants and catalyst in the solution, and the maximum time allowed for completion of the reaction, and can be readily determined by routine experimentation. In typical embodiments, a suitable mole ratio of the catalyst metal, nickel or palladium, to arylhalide is in the range of 1:1000 to 1:10.

The mole ratio of the cocatalyst to the arylmetal reagent to be reacted is not critical, but should be a catalytic ratio less than 1:2 and preferably about 1:4 or less. The mole ratio of the cocatalyst to the catalyst is not critical and a suitable ratio can be determined by routine experimentation. In typical embodiments, a suitable mole ratio of the cocatalyst to catalyst is in the range of 25:1 to 1:1.

In typical embodiments, the reaction is suitably conducted at a temperature of from about 20° C. to 100° C., although higher temperature may be used in some embodiments.

The order of addition of the reaction components is not critical when the arylhalide does not bear a substituent that is reactive to the arylmetal reagent. All the reaction components may be mixed at a temperature below that at which reaction occurs, in any order, and then heated to the reaction temperature. Alternatively, one or more of the components may be added to a mixture of the other components that is at the desired reaction temperature. For larger scale operation of the process, it is generally preferred to gradually add either the arylmetal reagent or the arylhalide to a mixture of the other components at the desired reaction temperature in order to control the exothermic heat release of the reaction by the rate of the addition.

When the arylhalide does bear a substituent that is reactive to the arylmetal reagent, the order of addition should preferably favor minimizing the reaction of the substituent with the arylmetal reagent. Preferably, the arylhalide and the arylmetal reagent should not be in mixture in the absence of the catalyst system under conditions where the substituent will react. Also, the biaryl product bearing the substituent should preferably not be in mixture with a large excess of the arylmetal reagent, as would occur during a gradual addition of the arylhalide to a mixture of the other components at the desired reaction temperature. Typically, the most preferred order of addition is to add the arylmetal reagent to a mixture of the arylhalide and the catalyst system that is at the desired reaction temperature. In this mode, the concentration of the catalyst system components, the length of time for the gradual addition of the arylmetal reagent, the reaction temperature, and other reaction parameters are preferably optimized to maximize the reaction selectivity to the desired substituted biaryl compound and minimize the yield loss due to reactions of the substituent.

The preferred order and manner of addition for any speciic embodiment can be determined by routine experimentation with a view towards both reaction performance and chemical engineering considerations.

The desired biaryl compound is recovered by known methods.

The present invention specifically provides a process for the preparation of 2-(4'-methylphenyl)benzonitrile comprising reacting a 4-methylphenylmagnesium reagent with 2-halobenzonitrile in the presence of a catalyst system comprising a catalyst selected from nickel catalysts and palladium catalysts and a zinc cocatalyst. The preferred 4-methylphenylnlagnesium reagent is 4-methylphenylmagnesium chloride, di(4-methylphenyl) magnesium or mixtures thereof. This preferred 4-methylphenylmagnesium reagent may be suitably prepared from 4-methylphenylchloride by its reaction with magnesium to form a 4-methylphenylmagnesium reagent.

The preferred 2-halobenzonitrile is, for economic reasons only, 2-chlorobenzonitrile, although 2-bromobenzonitrile is also quite suitable for a successful reaction.

The preferred catalyst for this application is provided by a nickel salt, preferably nickel bis(acetylacetonate), and a triorganophosphine or triorganophosphite ligand, preferably a trialkylphosphite, and preferably in a mole ratio of 1:1 to 4:1 phosphorus to nickel. The preferred catalyst for this application is a zinc halide salt, preferably zinc chloride or zinc bromide.

The reaction of 4-methylphenylmagnesium chloride with 2-chlorobenzonitrile in the presence of the catalyst is preferably conducted in tetrahydrofuran at a temperature of about 40 to 70° C.

In one practical embodiment, 4-methylphenylchloride in tetrahydrofuran is reacted with magnesium to form 4-methylphenylmagnesium chloride. This mixture is then combined with the 2-chlorobenzonitrile and the catalyst system components and reacted to form the 2-(4'-methylphenyl)benzonitrile.

EXAMPLES OF THE INVENTION

Without further elaboration, it is believed that one skilled in the art can, using the preceding description, utilize the present invention to its fullest extent. The following specific examples are intended merely to illustrate the invention and not to limit the scope of the disclosure or the scope of the claims in any way whatsoever.

Example 1
Preparation of 2-(4'methylphenyl)benzonitrile by zinc and nickel catalyzed reaction of 4-methylphenylmagnesium chloride with 2-chlorobenzonitrile:

A solution of 0.15 g (0.60 mmol) nickel acetylacetonate (moisture content<1%) and 0.082 g (0.60 mmol) zinc chloride in 3 mL of tetrahydrofuran was sequentially treated at room temperature with 11 μL (0.60 mmol) water, 0.31 mL (1.3 mmol) triisopropylphosphite, and 0.62 mL (1.1 mmol) of 1.73 M methylmagnesium chloride in tetrahydrofuran. The mixture was then treated with 1.38 g (10.0 mmol) of 2-chlorobenzonitrile and heated to 55° C. 7.32 mL (12.3 mmol) of 1.68 M 4-methylphenylmagnesium chloride in tetrahydrofuran was added to the mixture over the course of 1 h via a syringe pump. After the addition was complete, the reaction was stirred at 55° C. for an additional 15 minutes before a sample was withdrawn and quenched in a mixture of toluene and 1 N HCl. GC analysis of the hydrolyzed organic phase (using dodecane as an internal standard) showed the presence of 8.2 mmol of 2-(4'-methylphenyl)-benzonitrile (82% chemical yield based on 2-chlorobenzonitrile) and 0.36 mmol (3.6%) remaining 2-chlorobenzonitrile in the reaction mixture.

This Example illustrates the process of the instant invention wherein an unsymmetrical biaryl containing a functional group is prepared in high yield by reaction of an arylmagnesium reagent with a functionalized arylhalide in the presence of a catalyst system comprising a nickel catalyst and a zinc cocatalyst. This example also illustrates a nickel catalyst provided by combining ex situ a nickel salt, a ligand, and a reducing agent.

Comparative Example 1a
Attempted preparation of 2-(4'-methylphenyl)benzonitrile by nickel catalyzed reaction of 4-methylphenylmagnesium chloride with 2-chlorobenzonitrile:

The procedure was identical to Example 1, with the exception that no zinc chloride was added to the reaction. GC analysis of the hydrolyzed reaction sample taken after 15 minutes of reaction time at 55° C. showed the presence of 0.44 mmol of 2-(4'-methylphenyl)benzonitrile (44% chemical yield based on 2-chlorobenzonitrile) and 2.5 mmol (25%) remaining 2-chlorobenzonitrile in the reaction mixture. No other significant products were observed by the GC method.

This Example illustrates that the reaction of the arylmagnesium reagent with the chlorobenzonitrile in the presence of the nickel catalyst, but not the zinc cocatalyst, did not produce a high yield of the desired biarylnitrile. By comparison, Example 1 shows higher conversion of the chlorobenzonitrile (96% vs. 75%), higher selectivity towards the desired biarylnitrile (85% vs. 59%), and the resulting higher yield (82% vs. 44%) provided by the present invention wherein the zinc-cocatalyst is provided. Presumably, the missing balance of converted chlorobenzonitrile reacted with the arylmagnesium reagent at the nitrile group to give products that either did not partition into the organic layer of the hydrolyzed reaction sample or were too nonvolatile for detection by the GC method.

Comparative Example 1b
Attempted preparation of 2-(4'-methylphenyl)benzonitrile by nickel catalyzed reaction of 4-methylphenylmagnesium chloride with 2-chlorobenzonitrile in the presence stoichiometric zinc chloride:

The procedure was identical to Example 1, with the exception that 1.67 g (12.3 mmol; 1.0 equivalents relative to the 4-methyphenylmagnesium chloride) of zinc chloride was added to the reaction. GC analysis of the hydrolyzed reaction sample taken after 15 minutes of reaction time at 55° C. showed the presence of 0.18 mmol of 2-(4'-methylphenyl)benzonitrile (1.8% chemical yield based on 2-chlorobenzonitrile) and 8.6 mmol (86%) remaining 2-chlorobenzonitrile in the reaction mixture. No other significant products were observed by the GC method.

This Example illustrates that the reaction of the arylmagnesium reagent with the chlorobenzonitrile in the presence of the nickel catalyst and a stoichiometric amount of the zinc salt gave low conversion of the chlorobenzonitrile and did not produce any useful amount of the desired biarylnitrile. By comparison, Example 1 shows the high yield of biarylnitrile provided by the present invention wherein the zinc salt is provided in a catalytic amount.

Example 2
Preparation of 2-(4'-methylphenyl)benzonitrile by cadmium and nickel catalyzed reaction of 4-methylphenylmagnesium chloride with 2-chlorobenzonitrile:

The procedure was identical to Example 1, with the exception that 0.11 g (0.60 mmol) cadmium chloride was used instead of zinc chloride. GC analysis of the hydrolyzed reaction sample taken after 15 minutes of reaction time at 55° C. showed the presence of 7.5 mmol of 2-(4'-methylphenyl)benzonitrile (75% chemical yield based on 2-chlorobenzonitrile) and 0.94 mmol (9.4%) remaining 2-chlorobenzonitrile in the reaction mixture.

This Example illustrates the process of the present invention wherein a cadmium cocatalyst is provided in the place of the zinc cocatalyst of Example 1. Comparison to Comparative Example 1a shows the superior conversion, selectivity, and yield obtained when the cadmium cocatalyst is provided as compared to when neither a zinc nor a cadmium cocatalyst is provided.

Example 3
Preparation of 2-(4'-methylphenyl)benzonitrile by zinc and nickel catalyzed reaction of 4-methylphenylmagnesium chloride with 2-chlorobenzonitrile, using zinc powder to provide the cocatalyst.

A mixture of 0.15 g (0.60 mmol) nickel acetylacetonate (moisture content<1%) and 0.040 g (0.60 mmol) zinc powder in 3 mL of tetrahydrofuran was sequentially treated at room temperature with 0.31 mL (1.3 mmol) triisopropylphosphite and 1.38 g (10.0 mmol) of 2-chlorobenzonitrile. The mixture was then heated to 55° C. and 7.32 mL (12.3 mmol) of 1.68 M 4-methylphenylmagnesium chloride in tetrahydrofuran was added to it via a syringe pump over the course of 1 h. After the addition of the arylmagnesium reagent was complete, the reaction was stirred at 55° C. for an additional 15 minutes before a sample was withdrawn and quenched in a mixture of toluene and 1 N HCl. GC analysis of the hydrolyzed organic phase (using dodecane as an internal standard) showed the presence of 7.2 mmol of 2-(4'-methylphenyl)benzonitrile (72% chemical yield based on 2-chlorobenzonitrile) and 0.59 mmol (5.9%) remaining 2-chlorobenzonitrile in the reaction mixture.

This Example illustrates the process of the present invention wherein zinc metal is used to provide the zinc cocatalyst.

Example 4

Preparation of 4-(4'-methylphenyl)benzonitrile by zinc and nickel catalyzed reaction of 4-methylphenylmagnesium chloride with 4-chlorobenzonitrile:

The procedure was identical to Example 1, with the exception that 1.38 g (10.0 mmol) 4-chlorobenzonitrile was reacted instead of 2-chlorobenzonitrile. GC analysis of a hydrolyzed reaction sample after 15 minutes of reaction at 55° C. showed the presence of 7.5 mmol of 4-(4'-metlylphenyl)benzonitrile (75% chemical yield based on 4-chlorobenzonitrile) and 0.45 mmol (4.5%) remaining 4-chlorobenzonitrile in the reaction mixture.

Comparative Example 4

Attempted preparation of 4-(4'-methylphenyl)benzonitrile by nickel catalyzed reaction of 4-methylphenylmagnesium chloride with 4-chlorobenzonitrile:

The procedure was identical to Example 4, with the exception that no zinc chloride was added to the reaction. GC analysis of a hydrolyzed reaction sample showed the presence of 2.2 mmol 4-(4'-methylphenyl)benzonitrile (22% chemical yield based on 4-chlorobenzonitrile) and 1.7 mmol (17%) remaining 4-chlorobenzonitrile in the reaction mixture. No other significant products were observed by the GC method.

This Example again illustrates that the reaction of the arlymagnesium reagent with a chlorobenzonitrile in the presence of the nickel catalyst, but not the zinc cocatalyst, did not produce a high yield of the desired biarylnitrile. By comparison, Example 4 shows higher conversion of the chlorobenzonitrile (95% vs. 83%), higher selectivity towards the desired biarylnitrile (79% vs. 27%%), and the resulting higher yield (75% vs. 22%) provided by the present invention wherein the zinc-cocatalyst is provided. Presumably, the missing balance of converted chlorobenzonitrile reacted with the arylmagnesium reagent at the nitrile group to give products that either did not partition into the organic layer of the hydrolyzed reaction sample or were too nonvolatile for detection by the GC method. This comparison further illustrates the compatibility of the process of the instant invention with functional groups that are reactive to aryl Grignard reagents.

Example 5

Preparation of methyl 4-(4'-methylphenyl)benzoate by zinc and nickel catalyzed reaction of 4-methylphenylmagnesium chloride with methyl 4-chlorobenzoate:

A solution of 0.13 g (0.50 mmol) nickel acetylacetonate (moisture content<1%), 0.52 g (2.0 mmol) triphenylphosphine, 0.068 g (0.50 mmol) zinc chloride, and 9.0 µL (0.50 mmol) water was treated at room temperature with 0.30 mL (1.0 mmol) of 65 wt % (ca. 3.3 M) sodium bis(2-methoxyethoxy)aluminum dihydride in toluene. After stirring the dark colored solution for 15 minutes, 1.70 g (10.0 mmol) methyl 4-chlorobenzoate was added and the mixture heated to 550 C. The reaction mixture was then treated with 8.42 mL (14.2 mmol) of 1.68 M 4-methylphenylmagnesium chloride in tetrahydrofuran over the course of 1 h using a syringe pump. After the addition of the arylmagnesium reagent was complete, the reaction was stirred at 55° C. for an additional 15 minutes before a sample was withdrawn and quenched in a mixture of toluene and 1 N HCl. GC analysis of a hydrolyzed reaction sample (using dodecane as internal standard) showed the presence of 5.9 mmol of methyl 4-(4'-methylphenyl)benzoate (59% chemical yield based on methyl 4-chlorobenzoate) and 0.73 mmol (7.3%) remaining methyl 4-chlorobenzoate in the reaction mixture.

This Example illustrates the process of the present invention wherein an unsymmetrical biaryl compound containing a functional group can be prepared from reaction of an arylmagnesium reagent with a arylchloride bearing a function group (ester) which can otherwise react directly with the arylmagnesium reagent.

Comparative Example 5

Attempted preparation of methyl 4-(4'-methylphenyl) benzoate by nickel catalyzed reaction of 4-methylphenylmagnesium chloride with methyl 4-chlorobenzoate:

The procedure was identical to Example 5, with the exception that no zinc chloride was added to the reaction. GC analysis of a hydrolyzed reaction sample showed the presence of 3.4 mmol methyl 4-(4'-methylphenyl)benzoate (34% chemical yield based on methyl 4-chlorobenzoate) and 1.4 mmol (14%) remaining methyl 4-chlorobenzoate in the reaction mixture. No other significant reaction products were observed by the GC method.

This Example illustrates that the reaction of the arylmagnesium reagent with the chlorobenzoate ester in the presence of the nickel catalyst, but not the zinc cocatalyst, did not produce a good yield of the desired biarylcarboxylate ester. By comparison, Example 5 shows the higher yield (59% its. 34%) provided by the present invention wherein the zinc-cocatalyst is provided. Presumably, the missing balance of converted chlorobenzoate was consumed by reaction with the arylmagnesium reagent at the ester group to produce, after hydrolysis, a 1,1',1"-triarylcarbinol, which is too non-volatile for observation by the GC method. This comparison further illustrates the superior performance of the process of the instant invention for converting arylhalides with functional groups that are reactive to aryl Grignard reagents to corresponding functionalized biaryls.

Example 6

Preparation of ethyl 4-(4'-methylphenyl)benzoate by zinc amd nickel catalyzed reaction of 4-methylphenylmagnesium chloride with ethyl 4-iodobenzoate:

The procedure was identical to Example 5, with the exception that 2.76 g (10.0 mmol) of ethyl 4-iodobenzoate was reacted instead of methyl 4-chlorobenzoate. GC analysis of a hydrolyzed reaction sample showed the presence of 4.6 mmol of ethyl 4-(4'-methylphenyl)benzoate (46% chemical yield based on ethyl 4-iodobenzoate) and 0.04 mmol (0.4%) remaining ethyl 4-iodobenzoate in the reaction mixture.

This Example illustrates the process of the present invention wherein an unsymmetrical biaryl compound containing a functional group can be prepared from reaction of an aryl Grignard reagent with an aryliodide bearing a functional group (ester) which can otherwise react directly itself with the aryl Grignard reagent.

Comparative Example 6

Attempted preparation of ethyl 4-(4'-methylphenyl)benzoate by nickel catalyzed reaction of 4-methylphenylmagnesium chloride with ethyl 4-iodobenzoate:

The procedure was identical to Example 6, with the exception that no zinc chloride was added to the reaction. GC analysis of a hydrolyzed reaction sample showed the presence of 1.8 mmol of ethyl 4-(4'-methylphenyl)benzoate (18% chemical yield based on ethyl 4-iodobenzoate) and 0.28 mmol (2.8%) remaining ethyl 4-iodobenzoate in the reaction mixture.

This Example illustrates that the reaction of the arylmagnesium reagent with the iodobenzoate ester in the presence of the nickel catalyst, but not the zinc cocatalyst, did not produce a good yield of the desired biarylcarboxylate ester. By comparison, Example 6 shows the higher yield (46% vs. 18%) provided by the present invention wherein the zinc-cocatalyst is provided.

Example 7

Preparation of 4-(4'-chloropenyl)benzonitrile by zinc and nickel catalyzed reaction of 4-chlorophenylmagnesium bromide with 4-bromobenzonitrile:

A mixture of 26.7 g (1.10 mol) magnesium in 100 mL of tetrahydrofuran was treated at ambient temperature with ca. one-fifth of a solution of 172 g (0.900 mol) of 4-bromochlorobenzene in 800 mL of tetrahydrofuran. After the initial exotherm had subsided, the remainder of the solution of 4-bromochlorobenzene was added to the reaction mixture at a rate which maintained the temperature between 50–60° C. Upon completion of this addition, the reaction was heated for three additional hours at 50–60° C. The reaction mixture was then cooled to room temperature and the stirring stopped to allow the particulates to settle from the solution. Titration of the resultant dark, clear solution using the method of Watson and Eastham (*J. Organomet. Chem.*, vol. 9 (1967), p. 165) gave a concentration of 0.85 M for the contained 4-chlorophenylmagnesium bromide.

A solution of 3.02 g (22.2 mmol) zinc chloride and 5.70 g (22.2 mmol) nickel acetylacetonate (moisture content<1%) in 165 mL of tetrahydrofuran was sequentially treated at room temperature with 0.40 mL (22.2 mmol) water, 10.9 mL (44.4 mmol) triisopropylphosphite, and 27.4 mL (44.4 mmol) of 1.62 M methylmagnesium chloride in tetrahydrofuran. The resultant clear, dark reddish solution was then treated with 111.0 g (609.8 mniol) 4-bromobenzonitrile and cooled to 0° C. The reaction mixture was treated with 653 mL (555 mmol) of 0.85 M 4-chlorophenylmagnesium bromide over a 75 minute period, keeping the temperature below 10° C. After the addition of the arylmagnesium reagent was complete, the reaction was stirred at 0° C. for an additional hour before quenching was carried out by adding 550 mL of 1 M aqueous sodium citrate solution. After adding 300 mL of methyl t-butyl ether (MTBE), the reaction mixture was stirred vigorously at room temperature for 1 h while air was bubbled through the solution. The contents of the reaction flask were transferred into a separatory funnel, and flask rinsed with an additional 250 mL of MTBE. The lower green aqueous phase was drained off and the clear yellow organic phase was washed twice with 100 mL of brine. The crude solid product left after concentration was dissolved in 660 mL of chlorobenzene at 75° C., then 660 mL of heptane was added at a rate which maintained the temperature between 75–85° C. The clear yellow solution was then allowed to cool to ca. 40° C. and seeded with 1 mg of 4-(4'-chlorophenyl)benzonitrile. Crystallization commenced shortly after seeding, and the resultant slurry was cooled to 0–5° C. and stirred for 1 h. The solid product was filtered, washed with a small amount of heptane, and then dried under reduced pressure to afford 88.5 g (74.7%) of 4-(4'-chlorophenyl)benzonitrile as a fine white crystalline solid (m.p.=130.5–131.5° C.; identity confirmed by $^1$H- and $^{13}$C-NMR).

This Example illustrates an entire process of the present invention for the preparation of 4-(4'-chlorophenyl) benzonitrile from 4-bromobenzonitrile, including recovery of product. It further illustrates the use of ithe aryl magnesium substrate, instead of the functionalized arylhalide, as the limiting reagent in the process.

Example 8

Preparation of 3-amino-2-phenylpyridine by zinc and nickel catalyzed reaction of phenylmagnesium chloride with 3-amino-2-chloropyridine:

A solution of 0.643 g (5.00 mmol) 3-amino-2-chloropyridine, 0.164 g (0.250 mmol) dichlorobis (triphenylphosphine)nickel, and 0.170 g (1.25 mmol) zinc chloride in 5 mL of tetrahydrofuran was heated to 60° C. and treated with 8.12 mL (12.5 mmol) of 1.54 M phenylmagnesium chloride in tetrahydrofuran, dropwise, over 15 minutes. After the addition of the phenylmagnesium reagent was complete, the reaction was stirred at 60° C. for an additional 4 h before a sample was withdrawn and quenched in a mixture of toluene and aqueous 1 M Rochelle salt solution. GC analysis of the hydrolyzed organic phase (using dodecane as an internal standard) showed the presence of 2.90 mmol of 3-amino-2-phenylpyridine (58% chemical yield based on 3-amino-2-chloropyridine) and 0.23 mmol (4.7%) remaining 3-amino-2-chloropyridine in the reaction mixture.

This Example illustrates the preparation of a functionaliz, ed biaryl compound comprising a heterocyclic aryl group (pyridyl) by the process of the present invention. It also illustrates the use of a preformed, plhosphineligated nickel (II) compound to provide the catalyst.

Comparative Example 8

Attempted preparation of 3-amino-2-phenylpyridine by nickel catalyzed reaction of phenylmagnesium chloride with 3-amino-2-chloropyridine:

The procedure was identical to Example 8, with the exception that no zinc chloride was added to the reaction. GC analysis of the hydrolyzed reaction sample taken after 4 h of reaction time at 60° C. showed the presence cof 1.97 mmol of 3-amino-2-phenylpyridine (39% chemical yield based on 3-amino-2-chloropyridine) and 0.47 mmol (9.4%) remaining 3-amino-2-chloropyridine in the reaction mixture. No other significant products were observed by the GC method.

This Example illustrates that the reaction of the arylmagnesium reagent with the chloroaminopyridine in the presence of the nickel catalyst, but not the zinc cocatalyst, did not produce a good yield of the desired biarylamine. By comparison, Example 8 shows the higher yield (58% vs. 39%) provided by the present invention wherein the zinc-cocatalyst is provided. Presumably, the balance of consumed chloroaminopyridine that is not accounted for by the GC observable products was converted into derivatives which are too nonvolatile for observation by the GC method.

Example 9
Preparation of 4-(4'-methylphenyl)benzonitrile by zinc and nickel catalyzed reaction of 4-methylphenylmagnesium chloride with 4-bromobenzonitrile in pyridine solvent:

A solution of 0.128 g (0.500 mmol) nickel acetylacetonate (moisture content<1%) and 0.680 g (0.500 mmol) zinc chloride in 5 mL of pyridine was treated at room temperature with 1.82 g (10.0 mmol) 4-bromobenzonitrile. The resulting solution was heated to 55° C., then 7.32 mL (12.3 mmol) of 1.68 M 4-methylphenylmagnesium chloride in tetrahydrofuran was added via syringe pump over a 1 h period. After the addition of the arylmagnesium reagent was complete, the reaction was stirred at 55° C. for an additional 15 minutes before a sample was withdrawn and quenched in a mixture of toluene and 1 N HCl. GC analysis of the hydrolyzed organic phase (using dodecane as an internal GC standard) showed the presence of 4.5 mmol of 4-(4'-methylphenyl) benzonitrile (45% chemical yield based on 4-bromobenzonitrile) and 0.16 mmol (1.6%) remaining 4-bromobenzonitrile.

This Example illustrates the in situ generation of the active nickel catalyst from a nickel (II) salt and an aromatic nitrogen heterocyclic ligand, pyridine.

Example 10
Preparation of 2-(4'-methylphenyl)benzonitrile by zinc and palladium catalyzed reaction of 4-methylphenylmagnesium chloride with 2-bromobenzonitrile:

A solution of 0.91 g (5.0 mmol) 2-bromobenzonitrile, 0.034 g (0.25 mmol) zinc chloride, and 0.070 g (0.10 mmol) dichlorobis(triphenylphosphine)palladium in 5 mL tetrahydrofuran was heated to 60° C. and treated with 3.3 mL (5.5 mmol) of 1.68M 4-methylphenylmagnesium chloride in tetrahydrofuran, dropwise, over 15 minutes. After the addition of the arylmagnesium reagent was complete, the reaction was stirred at 60° C. for an additional 15 minutes before a sample was withdrawn and quenched in a mixture of toluene and 1 N HCl. GC analysis of the hydrolyzed organic phase (using dodecane as an internal standard) showed the presence of 4.3 mmol of 2-(4'-methylphenyl)benzonitrile (86% chemical yield based on 2-bromobenzonitrile), and no remaining 2-bromobenzonitrile in the reaction mixture.

This Example illustrates the process of the instant invention wherein an unsymmetrical biaryl containing a functional group is prepared in high yield by reaction of an arylmagnesium reagent with a functionalized arylbromide in the presence of a palladium catalyst and a zinc cocatalyst. It also illustrates the process using a preformed ligated palladium(II) compound to provide the palladium catalyst.

Comparison to the disclosure of International Patent Application PCT/IB97/00266 (International Publication Number WO 97/30970) shows that the zinc cocatalyst in the present invention provides good selectivity to the desired arylbenzonitrile even when the arylmagnesium halide is added relatively quickly, in this example over only 15 minutes.

Comparative Example 10a
Attempted preparation of 2-(4'-methylphenyl)benzonitrile by palladium catalyzed reaction of 4-methylphenylmagnesium chloride with 2-bromobenzonitrile:

The procedure was identical to Example 10, with the exception that no zinc chloride was added to the reaction. GC analysis of the hydrolyzed reaction sample taken after 15 minutes of reaction time at 60° C. showed the presence of 0.53 mmol of 2-(4'-methylphenyl)benzonitrile (11% chemical yield based on 2-bromobenzonitrile) and 1.0 mmol (20%) remaining 2-bromobenzonitrile in the reaction mixture. No other significant products were observed by the GC method.

This Example illustrates that the reaction of the arylmagnesium reagent with the bromobenzonitrile in the presence of the palladium catalyst, but not the zinc cocatalyst, did not produce a high yield of the desired biarylnitrile. By comparison, Example 10 shows higher conversion of the bromobenzonitrile (100% vs. 80%), much higher selectivity towards the desired biarylnitrile (86% vs. 14%), and the resulting much higher yield (86% vs. 11%) provided by the present invention wherein the zinc cocatalyst is provided. Presumably, the missing balance of converted bromobenzonitrile reacted with the arylmagnesium reagent at the nitrile group to give products that either did not partition into the organic layer of the hydrolyzed reaction sample or were too nonvolatile for detection by the GC method.

Comparative Example 10b
Attempted preparation of 2-(4'-methylphenyl)benzonitrile by palladium catalyzed reaction of 4-methylphenylmagnesium chloride with 2-bromobenzonitrile in the presence of stoichiometric zinc chloride:

The procedure was identical to Example 10, with the exception that 0.75 g (5.5 mmol; 1.0 equivalents relative to the arylmagnesium reagent) zinc chloride was added to the reaction. GC analysis of the hydrolyzed reaction sample taken after 15 minutes of reaction time at 60° C. showed the presence of 3.8 mmol of 2-(4'-methylphenyl)benzonitrile (76% chemical yield based on 2-bromobenzonitrile) and 0.08 mmol (1.6%) remaining 2-bromobenzonitrile in the reaction mixture.

This Example illustrates that the reaction of the arylmagnesium reagent with the bromobenzonitrile in the presence of the palladium catalyst and a stoichiometric amount of the zinc salt did not produce as high a yield of the desired biarylnitrile as when only a catalytic amount of zinc salt is provided (Example 10).

Example 11
Preparation of 2-(4'-methylphenyl)benzonitrile by zinc and palladium catalyzed reaction of 4-methylphenylmagnesium chloride with 2-bromobenzonitrile, using zinc acetate to provide the cocatalyst:

The procedure was identical to Example 10, with the exception that 0.046 g (0.25 g) zinc acetate was used instead of zinc chloride. GC analysis of the hydrolyzed reaction sample taken after 15 minutes of reaction time at 60° C. showed the presence of 4.5 mmol of 2-(4'-methylphenyl) benzonitrile (90% chemical yield based on 2-bromobenzonitrile) and no remaining 2-bromobenzonitrile in the reaction mixture.

This example illustrates the process of the present invention wherein the zinc cocatalyst is provided by another zinc salt, zinc acetate. Comparison with Example 10, using zinc chloride, shows an essentially similar result.

Example 12
Preparation of 2-(4'-methylphenyl)benzonitrile by zinc and palladium catalyzed reaction of 4-methylphenylmagnesium chloride with 2-bromobenzonitrile, using diethylzinc to provide the cocatalyst:

The procedure was identical to Example 10, with the exception that 0.23 mL (0.25 mmol) of 1.1 M diethylzinc in toluene was used instead of the zinc chloride. GC analysis of the hydrolyzed reaction sample taken after 15 minutes at 60° C. showed the presence of 4.2 mmol of 2-(4'- methylphenyl)benzonitrile (85% chemical yield based on 2-bromobenzonitrile) and no remaining 2-bromobenzonitrile in the reaction mixture.

This example illustrates the process of the present invention wherein the zinc cocatalyst is provided by a zinc compound, diethylzinc. Comparison with Examples 10 and 11, using zinc salts to provide the cocatalyst, shows an essentially similar result.

Example 13

Preparation of 2-(4"-methylphenyl)benzonitrile by cadmium and palladium catalyzed reaction of 4-methylphenylmagnesium chloride with 2-bromobenzonitrile:

The procedure was identical to Example 10, with the exception that 0.046 g (0.25 mmol) cadmium chloride was used instead of zinc chloride. GC analysis of the hydrolyzed reaction sample taken after 15 minutes at 60° C. showed the presence of 2.6 mmol of 2-(4'-methylphenyl)benzonitrile (52% chemical yield based on 2-bromobenzonitrile) and 0.66 mmol (13%) remaining 2-bromobenzonitrile in the reaction mixture.

This Example illustrates the process of the present invention wherein a cadmium cocatalyst is provided in the place of the zinc cocatalyst of Example 10, in combination with a palladium catalyst. Comparison to Comparative Example 10a shows the superior conversion, selectivity, and yield obtained when the cadmium cocatalyst is provided as compared to when neither a zinc nor a cadmium cocatalyst is provided.

Example 14

Preparation of 4-phenylbenzonitrile by zinc and palladium catalyzed reaction of phenylmagnesium chloride with 4-bromobenzonitrile:

The procedure was identical to Example 10, with the exceptions that 0.116 g (0.110 mmol) tetrakis (triphenylphosphine)palladium was used as the palladium source, 3.57 mL (5.50 mmol) of 1.54 M phenylmagnesium chloride was used as the arylmagnesium reagent, and 0.91 g (5.0 mmol) of 4-bromobenzonitrile was used as aryl halide substrate. GC analysis of the hydrolyzed reaction sample taken after 15 minutes of reaction time at 60° C. showed the presence of 4.7 mmol of 4-phenylbenzonitrile (94% chemical yield based on 4-bromobenzonitrile) and no remaining 4-bromobenzonitrile in the reaction mixture.

This Example illustrates the process of the present invention using a preformed ligated palladium(0) compound to provide the palladium catalyst.

Comparative Example 14

Attempted preparation of 4-phenylbenzonitrile by palladium catalyzed reaction of phenylmagnesium chloride with 4-bromobenzonitrile:

The procedure was identical to Example 14, with the exception that no zinc chloride was added to the reaction. GC analysis of the hydrolyzed reaction sample taken after 15 minutes of reaction time at 60° C. showed the presence of 3.0 mmol of 4-phenylbenzonitrile (60% chemical yield based on 4-bromobenzonitrile) and 0.07 mmol (1%) remaining 4-bromobenzonitrile in the reaction mixture. No other significant products were observed by the GC method.

This Example illustrates that the reaction of the arylmagnesium reagent with the bromobenzonitrile in the presence of the palladium catalyst, but not the zinc cocatalyst, did not produce as high yield of the desired biarylnitrile. By comparison, Example 14 shows the higher yield (94% vs. 60%) provided by the present invention wherein the zinc-cocatalyst is provided.

Example 15

Preparation of 4-phenylbenzonitrile by zinc and palladium catalyzed reaction of phenylmagnesium chloride with 4-chlorobenzonitrile:

The procedure was identical to Example 14, with the exceptions that 0.204 g (0.250 mmol) [1,1'-bis (diphenylphosphino)ferrocene] dichloropalladiuin·dichloromethane complex was used as palladium source and 0.688 g (5.00 mmol) 4-chlorobenzonitrile was used instead of 4-bromobenzonitrile. GC analysis of the hydrolyzed reaction sample taken after 15 minutes of reaction time at 60° C. showed the presence of 4.4 mmol of 4-phenylbenzonitrile (88% chemical yield based on 4-chlorobenzonitrile) and 0.03 mmol (0.6%) remaining 4-chlorobenzonitrile in the reaction mixture.

This Example illustrates the process of the present invention wherein an unsymmetrical biaryl compound is prepared from reaction of an arylmagnesium reagent with a arylchloride bearing a functional group (nitrile) which can otherwise react directly itself with the arylmagnesium reagent, in the presence of a palladium catalyst and a zinc cocatalyst. It also illustrates a palladium catalyst provided by a preformed palladium(II) compound comprising a bidentate phosphine ligand.

Comparative Example 15

Attempted preparation of 4-phenylbenzonitrile by palladium catalyzed reaction of phenylmagnesium chloride with 4-chlorobenzonitrile:

The procedure was identical to Example 15, with the exception that no zinc chloride was added to the reaction. GC analysis of the hydrolyzed reaction sample taken after 15 minutes of reaction time at 60° C. showed the presence of 0.41 mmol of 4-phenylbenzonitrile (8.2% chemical yield based on 4-chlorobenzonitrile) and 0.38% (7.6%) remaining 4-chlorobenzonitrile in the reaction mixture. No other significant products were observed by the GC method.

This Example illustrates that the reaction of the arylmagnesium reagent with the chlorobenzonitrile in the presence of the palladium catalyst, but not the zinc cocatalyst, did not produce a useful yield of the desired biarylnitrile. Presumably, nearly all the 4-chlorobenzonitrile reacted with the 4-methylphenylmagnesium chloride at the nitrile group to give products that either did not partition into the organic layer of the hydrolyzed reaction sample or were too nonvolatile for detection by the GC method. By comparison, Example 15 shows the useful high yield provided by the present invention wherein the zinc cocatalyst is provided (88% with the zinc cocatalyst vs. 8% without).

Example 16

Preparation of 4-(2'-furyl)benzonitrile by zinc and palladium catalyzed reaction of 2-furyllithium with 4-bromobenzonitrile:

A solution of 2-furyllithium was prepared using a procedure similar to that described by Perri, Rice, and Moore (*Org. Synth.*, vol. 69 (1990), p. 220). Thus, a solution of 0.44 mL (6.0 mmol) furan in 5 mL of tetrahydrofuran was cooled to 0° C. and treated with 3.44 mL (5.50 mol) of 1.60 M n-butyllithium. The reaction solution was stirred at 0° C. for 1 h, and then warmed to room temperature to complete the preparation of 2-furyllithium.

In a separate flask, a solution of 0.91 g (5.0 mmol) 4-bromobenzonitrile, 0.116 g (0.100 mmol) tetrakis (triphenylphosphine)palladium, and 0.034 g (0.25 mmol) zinc chloride in 5 mL of tetrahydrofuran was heated to 60° C. To this solution, the solution of 2-furyllithium was added dropwise over a period of 15 minutes. After the addition of the furyllithium reagent was complete, the reaction was stirred at 60° C. for an additional 15 minutes before a sample was withdrawn and quenched in a mixture of toluene and 1 N HCl. GC analysis of the hydrolyzed organic phase (using tridecane as an internal standard) showed the presence of 3.9 mmol of 4-(2'-furyl)benzonitrile (78% chemical yield based on 4-bromobenzonitrile) and 0.025 mmol (0.5%) remaining 4-bromobenzonitrile in the reaction mixture.

This Example illustrates the process of the present invention wherein an unsymmetrical biaryl prepared in high yield by reaction of an aryllithium reagent with an arylhalide in the presence of a palladium catalyst and a zinc cocatalyst. It also illustrates the preparation of an unsymmetrical biaryl compound comprising a heterocyclic aryl group (furyl) by the process of the present invention. It further illustrates a palladium catalyst provided by a preformed ligated palladium(0) compound.

Comparative Example 16

Attempted preparation of 4-(2'-furyl)benzonitrile by palladium catalyzed reaction of 2-furyllithium with 4-bromobenzonitrile:

The procedure was identical to Example 16, with the exception that no zinc chloride was added to the reaction. GC analysis of the hydrolyzed reaction sample taken after 15 minutes of reaction time at 60° C. showed the presence of 0.02 mmol of 4-(2'-furyl)benzonitrile (0.3% chemical yield based on 4-bromobenzonitrile) and no remaining 4-bromobenzonitrile in the reaction mixture. No other significant products were observed by the GC method.

This Example illustrates that the reaction of furyllithium reagent with the bromobenzonitrile in the presence of the palladium catalyst, but not the zinc cocatalyst, did not produce a useful yield of the furylbenzonitrile. Presumably, nearly all the bromobenzonitrile reacted with the furyllithium reagent at the nitrile group to give products that either did not partition into the organic layer of the hydrolyzed reaction sample or were too nonvolatile for detection by the GC method. By comparison, Example 16 shows the practical high yield of the furylbenzonitrile provided by the present invention wherein the zinc cocatalyst is provided (78% with the zinc cocatalyst vs.<1% without). This comparison further illustrates the compatibility of the process of the present invention with functional groups (nitrile, in this case) that are reactive to aryllithium reagents.

Example 17

Preparation of methyl 4-(4'-methylphenyl)benzoate by zinc and palladium catalyzed reaction of 4-methylphenylmagnesium chloride with methyl 4-bromobenzoate:

The procedure was identical to Example 10, with the exception that 1.08 g (5.00 mmol) methyl 4-bromobenzoate was reacted instead of 2-bromobenzonitrile. GC analysis of the hydrolyzed reaction sample taken after 15 minutes of reaction time at 60° C. showed the presence of 4.2 mmol of methyl 4-(4'-methylphenyl)benzoate (83% chemical yield based on methyl 4-bromobenzoate) and no remaining methyl 4-bromobenzoate in the reaction mixture.

This Example illustrates the process of the present invention wherein an unsymmetrical biaryl compound can be prepared from reaction of an arylmagnesium reagent with a arylbromide bearing another functional group (ester) which can otherwise react directly itself with the arylmagnesium reagent, in the presence of a palladium catalyst and a zinc cocatalyst.

Comparative Example 17

Attempted preparation of methyl 4-(4'-methylphenyl) benzoate by palladium catalyzed reaction of 4-methylphenylmagnesium chloride with methyl 4-bromobenzoate:

The procedure was identical to Example 17, with the exception that no zinc chloride was added to the reaction. GC analysis of the hydrolyzed reaction sample taken after 15 minutes of reaction time at 60° C. showed the presence of 3.0 mmol of methyl 4-(4'-methylphenyl)benzoate (60% chemical yield based on methyl 4-bromobenzoate) and 0.33 mmol (6.5%) remaining methyl 4-bromobenzoate in the reaction mixture. No other significant reaction products were observed by the GC method.

This Example illustrates that the reaction of the arylmagnesium reagent with the bromobenzoate ester in the presence of the palladium catalyst, without added zinc cocatalyst, did not produce as high a yield of the desired biarylcarboxylate ester. Presumably, the consumed benzoate ester that is not accounted for by the GC observable products was consumed by the typical reaction of two moles of arylmagnesium reagent with 1 mole of benzoate ester group to produce, after hydrolysis, a 1,1', 1"-triarylcarbinol, which is too nonvolatile for observation by the GC method. By comparison, Example 17 shows the higher yield of the desired biarylcarboxylate ester (83% vs. 60%) provided by the present invention wherein the zinc cocatalyst is provided.

Example 18

Preparation of ethyl 4-(4'-methylphenyl)benzoate by zinc and palladium catalyzed reaction of 4-methylphenylmagnesium chloride with ethyl 4-iodobenzoate:

The procedure was identical to Example 17, with the exceptions being that 1.38 g (5.00 mmol) ethyl 4-iodobenzoate was reacted instead of methyl 4-bromobenzoate and that the reaction temperature was kept between 25–30° C. during the addition of 4-methylphenylmagnesium chloride. GC analysis of the hydrolyzed reaction sample taken after 15 minutes of reaction time at 25° C. showed the presence of 4.3 mmol of ethyl 4-(4'-methylphenyl)benzoate (87% chemical yield based on ethyl 4-iodobenzoate) and no remaining ethyl 4-iodobenzoate in the reaction mixture.

This Example illustrates the process of the present invention wherein an unsymmetrical biaryl compound is prepared from reaction of an arylmagnesium reagent with an aryliodide bearing a functional group (ester) which can otherwise react directly itself with the arylmagnesinm reagent.

Comparative Example 18

Attempted preparation of ethyl 4-(4'-methylphenyl)benzoate by palladium catalyzed reaction of 4-methylphenylmagnesium chloride with ethyl 4-iodobenzoate:

The procedure was identical to Example 18, with the exception that no zinc chloride was added to the reaction. GC analysis of the hydrolyzed reaction sample taken after 15 minutes of reaction time at 25° C. showed the presence of 3.2 mmol of ethyl 4-(4'-methylphenyl)benzoate (64% chemical yield based on ethyl 4-iodobenzoate) and 0.46 mmol (9.2%) remaining ethyl 4-iodobenzoate in the reaction mixture. No other significant reaction products were observed by the GC method.

This Example illustrates that the reaction of the arylmagnesium reagent with the iodobenzoate ester in the presence of the palladium catalyst, without added zinc cocatalyst, did not produce as high a yield of the desired biarylcarboxylate ester. By comparison, Example 18 shows the higher yield of the desired biarylcarboxylate ester (87% vs. 64%) provided by the present invention wherein the zinc cocatalyst is provided.

Example 19
Preparation of 4-(4'-methylphenyl)propiophenone by zinc and palladium catalyzed reaction of 4-methylphenylmagnesium chloride with 4-bromopropiophenone:

A solution of 1.06 g (5.00 mmol) 4-bromopropiophenone, 0.170 g (1.25 mmol) zinc chloride, and 0.175 g (0.25 mmol) dichlorobis(triphenylphosphine) palladium in 5 mL of tetrahydrofuran was heated to 60° C. and treated with 3.72 mL (6.25 mmol) of 1.68 M 4-methylphenylmagnesium chloride in tetrahydrofuran, dropwise, over a 15 minutes. After the addition of the arylmagnesium reagent was complete, the reaction was stirred at 60° C. for an additional 15 minutes before a sample was withdrawn and quenched in a mixture of toluene and 1 N HCl. GC analysis of the hydrolyzed organic phase (using tridecane as an internal standard) showed the presence of 2.4 mmol of 4-(4'-methylphenyl)propiophenone (48% chemical yield based on 4-bromopropiophenone), 0.69 mmol of 1-(4-methylphenyl)-1-(4-bromophenyl)propanol (14% chemical yield based on 4-bromopropiophenone), and 0.43 mmol (8.6%) remaining 4-bromopropiophenone in the reaction mixture.

This Example illustrates the process of the present invention wherein an unsymmetrical biaryl compound is prepared by reaction of an arylmagnesium reagent with an arylbromide bearing another functional group (ketone) which can react directly with the arylmagnesium reagent. In this case, the GC analysis also detects the product of the reaction of the functional group with the arylmagnesium reagent, 1-(4-methylphenyl)-1-(4-bromopheonyl)propanol.

Comparative Example 19
Attempted preparation of 4-(4'-methylphenyl)propiophenone by palladium catalyzed reaction of 4-methylphenylmagnesium chloride with 4-bromopropiophenone:

The procedure was identical to Example 19, with the exception that no zinc chloride was added to the reaction. GC analysis of the hydrolyzed reaction sample taken after 15 minutes of reaction time at 60° C. showed the presence of 1.2 mmol of 4-(4'-methylphenyl)propiophenone (24% chemical yield based on 4-bromopropiophenone), 1.4 mmol of 1-(4-methylphenyl)-1-(4-bromophenyl)propanol (27% chemical yield based on 4-bromopropiophenone), and 1.0 mmol (21%) remaining 4-bromopropiophenone.

This Example illustrates that the reaction of the arylmagnesium reagent with the bromophenyl alkyl ketone in the presence of the palladium catalyst, but not the zinc cocatalyst, did not produce as high a yield of the desired biaryl alkyl ketone. Instead, the reaction produced a significantly higher level of the product of the direct addition of the arylmagnesium reagent with the keto group. By comparison, Example 19 shows higher conversion of the bromophenyl alkyl ketone (91% vs. 79%), higher selectivity towards the desired biaryl alkyl ketone (53% vs. 30%), and the resulting higher yield (48% vs. 24%) provided by the present invention wherein the zinc cocat;alyst is present in the reaction.

Example 20
Preparation of 3-cyano-5-phenylpyridine by zinc and palladium catalyzed reaction of phenylmagnesium chloride with 3-cyano-5-bromopyridine:

The procedure was identical to Example 10, with the exceptions that 3.44 mL (5.50 mmol) of 1.60 M phenylmagnesium chloride in tetrahydrofuran was used as the arylmagnesium reagent and 0.915 g (5.00 mmol) of 3-cyano-5-bromopyridine was used as the aryl halide substrate. GC analysis of the hydrolyzed reaction sample taken after 145 minutes of reaction time at 60° C. showed the presence of 4.57 mmol of 3-cyano-5-phenylpyridine (92% chemical yield based on 3-cyano-5-bromopyridine) and 0.11 mmol (2.2%) remaining 3-cyano-5-bromopyridine in the reaction mixture.

This example illustrates the process of the present invention for the preparation of a functionalized biaryl compound comprising a heterocyclic aryl group (pyridyl) bearing a functional group (nitrile) that can react directly with the arylmagnesium reagent, using a palladium catalyst and a zinc cocatalyst.

Comparative Example 20
Attempted preparation of 3-cyano-5-phenylypridine by palladium catalyzed reaction of phenylmagnesium chloride with 3-cyano-5-bromopyridine:

The procedure was identical to Example 21, with the exception that no zinc chloride was added to the reaction. GC analysis of the hydrolyzed reaction sample taken after 15 minutes of reaction time at 60° C. showed the presence of 2.71 mmol of 3-cyano-5-phenylpyridine (54% chemical yield based on 3-cyano-5-bromopyridine) and 0.05 mmol (1.0%) remaining 3-cyano-5-bromopyridine in the reaction mixture. No other significant products were observed by the GC method.

This example illustrates that the reaction of the arylmagnesium reagent with the cyanobromopyridine in the presence of the palladium catalyst, but not the zinc cocatalyst, did not produce as high a yield of the desired biarylnitrile. Presumably, the undetected balance of the starting cyanobromopyridine reacted with the arylmagnesium reagent at the nitrile group to give products that either did not partition into the organic layer of the hydrolyzed reaction sample or were too nonvolatile for detection by the GC method. By comparison, Example 20 shows the higher yield of the desired biarylnitrile (92% vs. 54%) provided by the present invention wherein the zinc cocatalyst is provided to the reaction.

Example 21
Preparation of 3-cyano-2-(4'methylphenyl)pyridine by zinc and nickel catalyzed reaction of 4-methylphenylmagnesium chloride with 2-chloro-3-cyanopyridine:

The procedure was identical to Example 1, with the exception that 1.38 g (10.0 mmol) 2-chloro-3-cyanopyridine was reacted instead of 2-chlorobenzonitrile. GC analysis of a hydrolyzed reaction sample after 15 minutes of reaction at 55° C. showed the presence of 8.5 mmol of 3-cyano-2-(4'-methylphenyl)pyridine (85% chemical yield based on 2-chloro-3-cyanopyridine and no remaining 2-chloro-3-cyanopyridine.

This example illustrates the process of the present invention for the preparation of a functionalized biaryl compound comprising a heterocyclic aryl group (pyridyl) bearing a functional group (nitrile) that can react directly with the arylmagnesium reagent using a nickel catalyst and a zinc cocatalyst.

Example 22
Preparation of 2-(4'-methylphenyl)benzonitrile by zinc and nickel catalyzed reaction of 4-methylphenylmagnesium chloride with 2-chlorobenzonitrile:

A solution of 0.137 g (0.200 mmol) [1,1'-bis(diphenylphosphino)-ferrocene]dichloronickel, 0.068 g (0.50 mmol) zinc chloride, arld 1.38 g (10.0 mmol) of 2-chlorobenzonitrile in 4 mL of tetrahydrofuran was heated to 55–60° C. and treated with 7.53 mL (12.5 mmol) of 1.66 M 4-methylphenylmagnesium chloride in tetrahydrofuran over 20 minutes. After the addition of the arylmagnesium reagent was complete, the reaction was stirred at 55–60° C. for an additional 15 minutes before a sample was withdrawn and quenched in a mixture of toluene and 3 N HCl. GC analysis of the hydrolyzed organic phase (using tridecane as an internal standard) showed the presence of 8.3 mmol of 2-(4'-methylphenyl)benzonitrile (83% chemical yield based on 2-chlorobenzonitrile) and no remaining 2-chlorobenzonitrile in the reaction mixture.

This Example illustrates the process of the present invention wherein an unsymmetrical biaryl is prepared in high yield by reaction of an arylmagnesium reagent with a functionalized arylchloride in the presence of a nickel catalyst and a zinc cocatalyst. It also illustrates a nickel catalyst provided by a nickel(II) compound, and a nickel catalyst comprising a bidentate phosphine ligand.

Comparative Example 22a
Attempted preparation of 2-(4'-methylphenyl)benzonitrile by nickel catalyzed reaction of 4-methylphenylmagnesium chloride with 2-chlorobenzonitrile:

The procedure was identical to Example 23, with the exception that no zinc chloride was added to the reaction. GC analysis of the hydrolyzed reaction sample taken after 15 minutes of reaction time at 55–60° C. showed the presence of 3.9 mmol of 2-(4'-methylphenyl)benzonitrile (39% chemical yield based on 2-chlorobenzonitrile) and 0.67 mmol (6.7%) remaining 2-chlorobenzonitrile in the reaction mixture. No other significant products (>10 area %) were observed by the GC method.

This Example illustrates that the reaction of the arylmagnesium reagent with the chlorobenzonitrile in the presence of the nickel catalyst, but not the zinc cocatalyst, did not produce a high yield of the desired biarylnitrile. By comparison, Example 22 shows the higher yield of the desired biarylnitrile (83% vs. 39%) provided by the present invention wherein the zinc cocatalyst is provided.

Comparative Example 22b
Attempted preparation of 2-(4'-methylphenyl)benzonitrile by zinc catalyzed reaction of 4-methylphenylmagnesium chloride with 2-chlorobenzonitrile:

The procedure was identical to Example 22, with the exception that no nickel catalyst was added to the reaction. GC analysis of the hydrolyzed reaction sample taken after 15 minutes of reaction time at 55–60° C. showed the presence of 1.7 mmol (17%) remaining 2-chlorobenzonitrile and no 2-(4'-methylphenyl)benzonitrile in the reaction mixture. No other significant products (>10 area %) were observed by the GC method.

This Example illustrates that the reaction of the arylmagnesium reagent with the chlorobenzonitrile in the presence of the zinc cocatalyst, but not the nickel catalyst, did not produce the desired biarylnitrile. Instead most of the chlorobenzonitrile was consumed to make products that either did not partition into the organic layer of the hydrolyzed reaction sample or were too nonvolatile for detection by the GC method.

Example 23
Preparation of 2-(4'-methylphenyl)benzonitrile by zinc and nickel catalyzed reaction of 4-methylphenylmagnesium chloride with 2-chlorobenzonitrile:

The procedure was identical to Example 22, with the exception that the nickel catalyst was prepared in situ from a mixture of 0.051 g (0.20 mmol) nickel acetylacetonate and 0.122 g (0.22 mmol) 1,1'-bis(diphlenylphosphino)ferrocene. GC analysis of the hydrolyzed reaction sample taken after 15 minutes of reaction time at 55–60° C. showed the presence of 8.5 mmol of 2-(4'-methylphenyl)benzonitrile (85% chemical yield based on 2-chlorobenzonitrile) and <0.05 mmol (<0.5%) remaining 2-chlorobenzonitrile in the reaction mixture.

This Example illustrates the process of the present invention wherein the nickel catalyst is provided in situ by a nickel salt and bidentate phosphine ligand.

The present invention has been shown by both description and examples. The Examples are only examples and cannot be construed to limit the scope of the invention. One of ordinary skill in the art will envision equivalents to the inventive process described by the following claims which are within the scope and spirit of the claimed invention.

We claim as our invention:

1. A process for the preparation of an biaryl compound of the formula Ar-Ar' comprising reacting an arylmetal reagent selected from arylmagnesium reagents and aryllithium reagents, wherein the aryl group is Ar, with an arylhalide of the formula Ar'X, wherein X is a halide, in the presence of a catalyst system consisting essentially of a catalyst selected from nickel catalysts and palladium catalysts and a cocatalyst selected from zinc cocatalysts and cadmium cocatalysts, and wherein the cocatalyst is present at a mole ratio of cocatalyst to aryl metal reagent of less than 1:4 and the mole ratio of cocatalyst to catalyst is in the range of 25:1 to 1:1.

2. The process of claim 1 wherein the cocatalyst is a zinc cocatalyst provided by a zinc salt, a zinc compound, zinc metal, or mixtures thereof.

3. The process of claim 1 wherein the zinc cocatalyst is provided by a zinc halide salt.

4. The process of claim 1 wherein the arylmetal reagent is an arylmagnesium halide.

5. The process of claim 1 wherein the catalyst is a nickel catalyst selected from catalysts provided by nickel(0) compounds, catalysts provided by nickel(II) compounds, and catalysts provided by nickel(II) salts.

6. The process of claim 5 wherein the catalyst comprises a ligand selected from monodentate, bidentate, and tridentate ligands which comprise a ligating atom selected from nitrogen and phosphorus.

7. The process of claim 1 wherein the catalyst is a palladium catalyst selected from catalysts provided by palladium(0) compounds, catalysts provided by palladium (II) compounds, and catalysts provided by palladium(II) salts.

8. The process of claim 7 wherein the catalyst comprises a ligand selected from monodentate, bidentate, and tridentate ligands which comprise a ligating atom selected from nitrogen and phosphorus.

9. A process for the preparation of 2-(4'-methylphenyl) benzonitrile comprising reacting a 4-methylphenylmagnesium reagent with a 2-halobenzonitrile in the presence of a catalyst system a consistently essentially of a catalyst selected from nickel catalysts and palladium catalysts and a zinc cocatalyst, and wherein the cocatalyst is present at a mole ratio of cocatalyst to 4-methylphenyl magnesium reagent of less than 1:4 and the mole ratio of cocatalyst to catalyst is in the range of 25:1 to 1:1.

10. The process of claim 9 wherein the 4-methylphenylmagnesium reagent is a 4-methylphenylmagnesium halide.

11. The process of claim 9 wherein the 4-methylphenylmagnesium reagent is a 4-methylphenylmagnesium chloride and the 2-halobenzonitrile is 2-chlorobenzonitrile.

12. The process of claim 9 wherein the zinc cocatalyst is provided by a zinc salt, a zinc compound, zinc metal, or mixtures thereof.

13. The process of claim 9 wherein the zinc cocatalyst is provided by a zinc halide salt.

14. The process of claim 9 wherein the catalyst is a nickel catalyst selected from catalysts provided by nickel(0) compounds, catalysts provided by nickel(II) compounds, and catalysts provided by nickel(II) salts.

15. The process of claim 14 wherein the catalyst comprises a ligand selected from monodentate, bidentate, and tridentate ligands which comprise a ligating atom selected from nitrogen and phosphorus.

16. The process of claim 15 wherein the nickel catalyst is provided by nickel bis(acetylacetonate) and comprises a trialkylphosphite ligand.

17. In the process for the preparation of biaryl compounds by reacting an arylmetal reagent selected for arylmagnesium reagents and aryllithium reagents with an arylhalide in the presence of a catalyst selected from nickel catalysts and palladium catalysts, the improvement wherein the reaction mixture further consists essentially of a cocatalyst selected from zinc cocatalysts and cadmium cocatalysts, said cocatalyst being present at a mole ratio of cocatalyst to arylmetal reagent of less than 1:4 and with the mole ratio of cocatalyst to catalyst being in the range of 25:1 to 1:1.

* * * * *